United States Patent [19]
Chen et al.

[11] Patent Number: 5,690,930
[45] Date of Patent: Nov. 25, 1997

[54] DNA ENCODING THE HEME-REGULATED EUKARYOTIC INITIATION FACTOR 2α KINASE

[75] Inventors: Jane-Jane Chen, Belmont; Irving M. London, Cambridge, both of Mass.

[73] Assignee: Massachusetts Institute of Technology, Cambridge, Mass.

[21] Appl. No.: 630,524

[22] Filed: Apr. 10, 1996

Related U.S. Application Data

[62] Division of Ser. No. 938,782, Aug. 31, 1992, Pat. No. 5,525,513.

[30] Foreign Application Priority Data

Mar. 2, 1992 [JP] Japan ................................ 4-081664

[51] Int. Cl.$^6$ ................................................ A61K 38/45
[52] U.S. Cl. ............................................... 424/94.5
[58] Field of Search ........................... 435/194; 424/94.5

[56] References Cited

U.S. PATENT DOCUMENTS

| | | | |
|---|---|---|---|
| 4,594,319 | 6/1986 | Sharma | 435/7.23 |
| 4,683,195 | 7/1987 | Mullis et al. | 435/6 |
| 5,002,874 | 3/1991 | Kaufman | 435/69.1 |

OTHER PUBLICATIONS

Chen J.-J. et al., "Cloning of the cDNA of the heme-regulated eukaryotic initiation factor 2 alpha (eIF-2 alpha) kinase of rabbit reticulocytes: homology to yeast GCN2 protein kinase and human double-stranded-RNA-dependent eIF-2 alpha kinase" *Proc. Natl. Acad. Sci. USA* 88:7729-7733 (Sep. 1991).

Yang, J., et al., "Structure-function study of heme-regulated eukaryotic initiation factor 2 alpha kinase by site-directed mutagenesis" *J. Cell Biol.* 115:435A (Nov. 1991).

Chen, J.-J., et al., "Amino-acid microsequencing of internal tryptic peptides of heme-regulated eukaryotic initiation factor 2 alpha subunit kinase: homology to protein kinases" *Proc. Natl. Acad. USA* 88:315-319 (Jan. 1991).

Mendez, R., et al., "Regulation of heme-controlled eukaryotic polypeptide chain-initiation factor 2 alpha-subunit kinase of reticulocyte lysates" *J. Biol. Chem.* 267:11500-11507 (5 Jun. 1992).

Chen, J-J., et al., "Disulfide Bond Formation in the Regulation of eIF-2α Kinase by Heme"; *J. Biol. Chem.*, 264:9559-9564 (1989).

Cigan, A.M., et al., "Yeast Translation Initiation Suppressor sui2 Encodes the αSubunit of Eukaryotic Initiation Factor 2 and Shares Sequence Identity with the Human α Subunit," *Proc. Natl. Acad. Sci. USA*, 86:2784-2788 (1989).

Dever, T.E., et al., "Phosphorylation of Initiation Factor 2α by Protein Kinase GCN2 Mediates Gene-Specific Translational Control of GCN4 in Yeast," *Cell*, 68, 585-596 (1992).

Ernst, H., et al., "Cloning and Sequencing of Complementary DNAs Encoding to α-Subunit of Translational Initiation Factor eIF-2," *J. Biol. Chem.*, 262:1206-1212 (1987).

Fawcett, T.W., et al., "An Effective Method for Eliminating 'Artifact Banding' When Sequencing Double-Stranded DNA Templates," *BioTechniques*, 9:46-48 (1990).

Felger, P.L., et al., "Lipofection: A Highly Efficient, Lipid-mediated DNA-Transfection Procedure", *Proc. Natl. Acad. Sci.*, 84:7413-7417 (1987).

Frohman, M.A., et al., "Rapid Production of Full-length cDNAs from Rare Transcripts: Amplification Using a Single Gene-specific Oligonucleotide Primer," *Proc. Natl. Acad. Sci. USA*, 85, 8998-9002 (1988).

Gallie, D.R., et al., "A Comparison of Eukaryotic Viral 5'-Leader Sequences as Enhancers of mRNA Expression In Vivo," *Nucl. Acids Res.*, 15, 8693-8711 (1987).

Gehrke, L., et al., "In: McCarthy, JEG Post-Transcriptional Regulation of Gene Expression, Series H: Cell Biology, ed. Tuite, M. (Springer Verlag Berlin)", 49:389-398 (1990).

Hanks, S.K., et al., "The Protein Kinase Family: Conserved Features and Deduced Phylogeny of the Catalytic Domains," *Science*, 241:42-52 (1988).

Maizel, J.V., Jr., et al., "Enhanced Graphic Matrix Analysis of Nucleic Acid and Protein Sequences," *Proc. Natl. Acad. Sci., USA* 78:7665-7669 (1981).

Maniatis, T., et al., *Molecular Cloning*, Cold Spring Harbor Laboratory Press (1989).

Meurs, E., et al., "Molecular Cloning and Characterization of the Human Double-Stranded RNA-Activated Protein Kinase Induced by Interferon," *Cell*, 62:379-390 (1990).

Miller, A.D., et al., "Improved Retroviral Vectors for Gene Transfer and Expression," *BioTechniques*, 7:980-990 (1989).

(List continued on next page.)

*Primary Examiner*—Robert A. Wax
*Assistant Examiner*—Gabriele E. Bugalsky
*Attorney, Agent, or Firm*—Arnall Golden & Gregory

[57] ABSTRACT

The cDNA which encodes heme-regulated eIF-2α kinase (HRI) has been cloned from a lambda Zap II cDNA library of rabbit reticulocytes. The rabbit HRI cDNA is highly homologous to human HRI and hybridizes to the human HRI DNA under moderately stringent conditions. The rabbit HRI cDNA contains 2729 amino acids. In vitro translation of HRI mRNA transcribed from HRI cDNA yields a 90 kDa polypeptide with eIF-2α kinase activity. Since HRI is a potent inhibitor of protein synthesis, it is anti-proliferative in nature. In addition, the unusually high degree of homology of HRI to three protein kinases involved in the regulation of cell division suggests that HRI plays a direct role in the regulation of cell division. Since regulation of protein synthesis is vital for cell growth and differentiation, the cDNA can be inserted into cells to manipulate proliferation and differentiation, especially of cells that are proliferating in an uncontrolled manner or characterized by arrested differentiation, such as some of the types of cancers. Initiation of protein synthesis can also be regulated by another eIF-2α kinase which is activated by double-stranded RNA (dsI) which represents an interferon-mediated response to viral infection. Deletion mutants of HRI cDNA can be constructed that are insensitive to regulation by heme, which should be more effective than native HRI in its anti-viral and anti-proliferative action.

12 Claims, 6 Drawing Sheets

OTHER PUBLICATIONS

Pal, J.K., et al., "Tissue Distribution and Immunoreactivity of Heme–regulated eIF–1α Kinase Determined by Monoclonal Antibodies," *Biochem.* 30:2555–2562 (1991).

Patkak, V.K., et al., "Generation of a Mutant Form of Protein Synthesis Initiation Factor eIF–2 Lacking the Site of Phosphorylation by eIF–2 Kinases," *Mol, Cell. Biol.*, 8:993–995 (1988).

Pearson, W.R., et al., "Improved Tool for Biological Sequence Comparison," *Proc. Natl. Acad. Sci. U.S.A.* 85:2444–2448 (1988).

Sanger, F., et al., "DNA Sequencing with Chain–terminating Inhibitors," *Proc. Natl. Acad. Sci., USA,* 74:5463–5467 (1977).

Tzamarias, D., et al., and Tzamarias, et al., *Cell,* 57:947–954 (1989).

Ullrich, A., et al., "Signal Transduction by Receptors with Tyrosine Kinase Activity," *Cell,* 61:302–212 (1990).

Wilson, J.M., et al., "Implantation of Vascular Grafts Lined With Genetically Modified Endothelial Cells", *Science,* 244:1344–1346 (1980).

Barnes, et al., "Human DNA ligase I cDNA: Cloning and functional expression in Saccharomyces cerevisae," *Proc. Natl. Acad. Sci. USA* 87:6679–6683 (1990).

Becker, et al., "A cDNA encoding a human CCAAT–binding protein cloned by functional complement in yeast," *Proc. Natl. Acad. Sci. USA* 88:1968–1972 (1991).

Benedetti and Baglioni, "Activation of Hemin–regulated Initiation Factor–2 Kinase in Heat–shocked HeLa Cells," *J. Biol. Chem.* 261:338–342 (1986).

Kranz and Holm, "Cloning by function: An alternative approach for identifying yeast homologs of genes from other organisms," *Proc. Natl. Acad. Sci. USA* 87:6629–6633 (1990).

Lee and Nurse, "Complementation used to clone a human homologue of the fission yeast cell cycle control gene cdc2," *Nature* 327:31–35 (1987).

Trachsel, et al., "Regulation of Protein Synthesis . . . " *Proc. Natl. Acad. Sci. USA* 75:3654–3658 (1978).

Wek, et al., "Juxtaposition of domains homologous to protein kinase and histidyl–tRNA synthetases in GCN2 protein suggests a mechanism for coupling GCN4 expression to amino acid availability," *Proc. Natl. Acad. Sci. USA* 86:4579–4583 (1989).

|  | | I | | II | III |
|---|---|---|---|---|---|
| CaMPK | 9/TEEYQLFEEL | GKGAFSVVRR | CVKVLAGQEY | AAKIINTKKL | SARDHQKLER | EARICRLLKH |
| HRI | 166/LNEFEELSIL | GKGGYGRVYK | VRNKLDGQYY | AIKKILIKGA | TKTDCMKVLR | EVKVLAGLQH |
| Src | 60/HEDVSLGELL | CKCNFGEVYK | GTLKDKTP.V | AVRTCKEDLP | .QELKIKFLQ | EAKILKQYDH |

|  | IV | | | V | | |
|---|---|---|---|---|---|---|
| CaMPK | PNIVRLHDSI | SEEGHH..... | ..YLIFDLVT | GGELFEDIVA | REYYSEAD.. | //..ASHCI |
| HRI | PNIVGYHTAW | IEHVHVHVQA | DRVPIQLPSL | EVLSDQEEDR | DQYGVKNDA | (138) ATKIF |
| Src | PNIVKLIGVC | TQRPV..... | ..YIIMELVP | GGDFLSFLRK | RKDELKLKQ. | //..LVRFS |

|  | | VI | | VII | | |
|---|---|---|---|---|---|---|
| CaMPK | QQILEAVLHQ | HQMGVVHRDL | KPENULLASK | LKGAAVKLAD | EGLAIEVEGE | QQAW...... |
| HRI | QELVEGVFYI | HNMGIVHRDL | KPRNIFLHGP | DQQ..VKIGD | EGLACADIIQ | KNAARTSRNG |
| Src | LDVAAGMLYL | EGKNCIHRDL | AARNOLVGEN | NT...LKISD | FGMSRQEDGG | VYSSS..... |

|  | | VIII | | IX | | |
|---|---|---|---|---|---|---|
| CaMPK | .....FGFA | GTPGYLSPEV | LRKDPYGKPV | DLWNCGVILY | ILLVGYPPFW | DEDQHRLYQQ |
| HRI | ERAPTHTSRV | GTCLYASPEQ | LEGSEYDAKS | DMYSVGVILL | ELFQPFGTEM | ERAEVLTGVR |
| Src | ......GLKQ | IPIKWTAPEA | LNYGRYSSES | DVWSFGILLW | ETFSLGVCPY | PGMTNQQARE |

|  | X | | | XI | | |
|---|---|---|---|---|---|---|
| CaMPK | IKAGAYDFPS | PEWDT..... | VTPEAKDLI | NKMLTINPSK | RITAAEEALKH | /210 |
| HRI | AGRIPDSLSK | RCPAQ (26) | FQNSAHVNU | TLQMKIIEQE | REIEELKKQL | /20 |
| src | QVERGYRMSA | PQN....... | CPEEIFTIM | MKCWDYKPEN | RPKFSDLHKE | /9 |

FIGURE 3

(A) Mouse uninduced | induced 3 4 5 days | Rabbit Reticulocyte (B) Human uninduced | induced | Rabbit Reticulocyte

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 2729 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rabbit
        ( G ) CELL TYPE: Reticulocytes ( i x ) FEATURE:
        ( A ) NAME/KEY: misc_feature
        ( B ) LOCATION: 113..2149
        ( D ) OTHER INFORMATION: /note= "Expression of HRI mRNA in Human erythroid cells, using as the probe rabbit HRI cDNA from nucleotides 113 to 2149."

( i x ) FEATURE:
        ( A ) NAME/KEY: misc_feature
        ( B ) LOCATION: 229..249
        ( D ) OTHER INFORMATION: /note= "Primer used in the amplification of human HRI cDNA sequence using the rabbit HRI cDNA sequence."

(ix) FEATURE:
  (A) NAME/KEY: misc_feature
  (B) LOCATION: 543..560
  (D) OTHER INFORMATION: /note= "Primer used in the amplification of human HRI cDNA sequence using the rabbit HRI cDNA sequence."

(ix) FEATURE:
  (A) NAME/KEY: misc_feature
  (B) LOCATION: 448..468
  (D) OTHER INFORMATION: /note= "Primer used in the amplification of human HRI cDNA sequence using the rabbit HRI cDNA sequence."

(ix) FEATURE:
  (A) NAME/KEY: misc_feature
  (B) LOCATION: 1009..1031
  (D) OTHER INFORMATION: /note= "Primer used in the amplification of a human HRI cDNA sequence using the rabbit HRI cDNA sequence."

(x) PUBLICATION INFORMATION:
  (A) AUTHORS: Chen, Jane J.
      London, Irving M.
  (B) TITLE: Cloning of the cDNA of the heme-regulated eukaryotic initiation factor 2alpha (eIF- 2alpha)kinase of rabbit reticulocytes: Homology to yeast GCN2 protein kinase and human double- stranded-RNA-dependent
  (C) JOURNAL: Proc. Natl. Acad. Sci. U.S.A.
  (D) VOLUME: 88
  (F) PAGES: 7729-7733
  (G) DATE: September-1991

(xi) SEQUENCE DESCRIPTION: SEQ ID NO:1:

```
CGCACGGCGC TCGCGACCCG GACGCGCGAG GAGGCGGTCC CGGAGTCGGG GAGCTGGCGG      60
GTGGGCTGTG GTCCCCGCAT TTGCGCGCGC GGGCGCCCGC GCGTGACCGG CGATGCTGGG     120
GGGCAGCGCC GGGACCCGCG GGGGCGAAGC CGAGGGCGAC GGGGCGGGGG CGGTGGGGGC     180
GGTGGCCCCG CCGCCCGCCA TCGACTTCCC CGCTGAGGTG TCGGATCCCA AGTATGACGA     240
GTCGGATGTC CCGGCAGAGC TGCAGGTGCT GAAGGAGCCG CTGCAGCAGC CAGCCTTCCC     300
CTTCGCCGTC GCCAACCAGC TGCTGCTCGT CTCCCTGCTG GAGCACCTGA GTCATGTGCA     360
CGAGCCAAAC CCGCTTCGCT CCAGACAGGT GTTTAAACTG CTCTGTCAGA CCTTCATCAA     420
AATGGGGCTG CTGTCTTCCT TCACCTGCAG CGACGAGTTT AGCTCATTGA GGCTGCATCA     480
CAACAGAGCT ATTACGCATC TGATGAGGTC CGCCAGAGAG AGAGTTCGGC AGGATCCCTG     540
TGCTGATAAT TCTCATATCC AGAAAATCAG GTCGCGAGAA GTTGCCTTGG AAGCACAGAC     600
CTCACGATAC TTGAATGAGT TTGAAGAGCT CTCCATCCTG GGGAAAGGTG GCTATGGCCG     660
AGTGTACAAG GTCAGGAATA AATTAGATGG CCAGTATTAT GCAATTAAAA AAATTCTGAT     720
TAAAGGTGCA ACTAAACAG ATTGCATGAA GGTATTACGA GAAGTGAAAG TGCTGGCGGG     780
CCTCCAGCAC CCTAATATCG TAGGCTATCA CACCGCGTGG ATAGAGCATG TCCACGTTCA     840
CGTTCAAGCA GACAGAGTTC CGATTCAGTT GCCTTCTCTG GAAGTGCTCT CTGACCAGGA     900
AGAAGACAGA GATCAATATG GTGTTAAAAA TGATGCAAGC AGCAGCTCAT CCATTATTTT     960
CGCTGAGTTC TCCCCAGAAA AAGAAAAATC CTCTGACGAA TGTGCCGTTG AGAGTCAGAA    1020
TAACAAACTG GTGAACTACA CCACCAACTT AGTGGTGAGG GACACCGGTG AGTTTGAATC    1080
GTCCACGGAG CGCCAAGAGA ACGGCTCGAT CGTGGAGCGT CAGCTACTGT TCGGGCATAA    1140
CTCAGACGTA GAAGAGGATT TCACGTCCGC GGAGGAATCT TCTGAGGAAG ACTTAAGCGC    1200
GTTGCGGCAC ACAGAGGTGC AGTACCACCT GATGCTGCAT ATCCAGATGC AGCTGTGCGA    1260
GCTGTCCCTG TGGGACTGGA TCGCCGAGAG GAACAGGCGG AGCCGAGAGT GCGTGGACGA    1320
```

| | | | | | |
|---|---|---|---|---|---|
| ATCTGCCTGT | CCTTATGTTA | TGGTCAGTGT | TGCAACAAAA | ATTTTTCAAG | AACTGGTGGA | 1380 |
| AGGTGTGTTT | TACATACATA | ACATGGGCAT | CGTGCACAGA | GACCTGAAGC | CTAGAAATAT | 1440 |
| TTTTCTTCAT | GGTCCTGATC | AACAAGTGAA | AATAGGAGAC | TTTGGTCTGG | CCTGCGCCGA | 1500 |
| CATCATCCAG | AAGAATGCGG | CCCGGACCAG | CAGAAACGGG | GAGAGAGCAC | CCACACACAC | 1560 |
| TTCCCGAGTG | GGCACCTGTC | TGTACGCCTC | GCCCGAGCAG | TTGGAAGGAT | CGGAGTATGA | 1620 |
| TGCCAAGTCA | GACATGTACA | GCGTCGGCGT | GATCCTGCTG | GAGCTCTTCC | AGCCCTTCGG | 1680 |
| GACAGAGATG | GAGCGGGCAG | AGGTCCTGAC | GGGCGTGCGA | GCTGGCCGCA | TACCCGACTC | 1740 |
| CCTCAGTAAG | AGGTGCCCGG | CGCAGGCCAA | GTACGTCCAG | CTGCTGACCA | GGAGGAACGC | 1800 |
| GTCCCAGCGG | CCGTCCGCCC | TTCAGCTGCT | GCAGAGTGAG | CTCTTCCAGA | ACTCCGCGCA | 1860 |
| TGTTAACCTC | ACCCTACAGA | TGAAGATAAT | AGAGCAGGAA | AGAGAAATCG | AGGAACTCAA | 1920 |
| GAAGCAGCTG | AGCCTCCTCT | CCCAGGCCCG | AGGGGTGAGG | AGTGACAGGC | GAGACGGAGA | 1980 |
| GCTCCCTGCC | TAGCCGTCAC | TCGGCCACGT | CACAGGGGAA | CGTGGACTTG | CACTTGCAGC | 2040 |
| AGTCAACTGG | AATGGACAAT | TTCAAGCCTC | CTGAGGTTCA | GGCGGCATAA | TCCTCACTTG | 2100 |
| GAATCACTCA | GCCCGCATGA | CTCTCCCCTC | ATGCTGCTCT | TCCCGGAGGT | ACCTCCTGGT | 2160 |
| GACCTCCTGG | TGACTGCTCC | CAATTAAACT | TACGCTTTTC | CCTTTCCTAT | TCCGCAAGTC | 2220 |
| CCATTCCTGA | GCCTCCTACC | TAAGCATTAA | CTAAATCTTA | GGTATCGGTC | TCCATTCTTT | 2280 |
| CTCCTTTGAA | TCCTGGCCAC | CTCGCTCCTT | TAGAAGCACA | CTCACTGCCC | CGCCACCACC | 2340 |
| CAAGGCCAGG | CCTGCACCCT | GGCGCAACAG | CTGCCAGTCT | TAGTCCTTAG | CTGCTGCTGC | 2400 |
| TGTTGCCAGA | GACACCTGCT | CCGTTCACTC | CCTCCAGGGT | GGAAGCTCAG | CCTGTGAGCA | 2460 |
| GCGCCTCTGC | TCTCCCCGGC | TGCAGCCCAG | CGCCACTCGG | GCAGGCTTCA | CACGCTCACC | 2520 |
| CCAGGTGGCC | TCGGAACAGC | TGCGACAGCA | TCTCCCCGCA | CCCTTCTGCC | TTCTCAGCAC | 2580 |
| TTGGCTCTCC | AGCCAGCCTC | TCCACTCACT | CGTTTTTGTT | TCCCGGAGCT | GTCTGCCACA | 2640 |
| ATGTTGGCAG | TCTTCATGGA | CTACTGTACG | TGATTCTGCT | GAATTTTAAA | TAAATAAACC | 2700 |
| CTGCAAATCA | AAAAAAAAA | AAAAAAAA | | | | 2729 |

( 2 ) INFORMATION FOR SEQ ID NO:2:

( i ) SEQUENCE CHARACTERISTICS:
        ( A ) LENGTH: 626 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rabbit
        ( G ) CELL TYPE: Reticulocytes ( i x ) FEATURE:
        ( A ) NAME/KEY: Peptide
        ( B ) LOCATION: 166..170
        ( D ) OTHER INFORMATION: /label= P- 56

( i x ) FEATURE:
        ( A ) NAME/KEY: Peptide
        ( B ) LOCATION: 454..459
        ( D ) OTHER INFORMATION: /label= P- 52

( i x ) FEATURE:

(A) NAME/KEY: Peptide
(B) LOCATION: 506..510
(D) OTHER INFORMATION: /label= P- 74

(xi) SEQUENCE DESCRIPTION: SEQ ID NO:2:

| Met | Leu | Gly | Gly | Ser | Ala | Gly | Thr | Arg | Gly | Gly | Glu | Ala | Glu | Gly | Asp |
|---|---|---|---|---|---|---|---|---|---|---|---|---|---|---|---|
| 1 | | | | 5 | | | | | 10 | | | | | 15 | |

| Gly | Ala | Gly | Ala | Val | Gly | Ala | Val | Ala | Pro | Pro | Pro | Ala | Ile | Asp | Phe |
|---|---|---|---|---|---|---|---|---|---|---|---|---|---|---|---|
| | | | 20 | | | | | 25 | | | | | 30 | | |

| Pro | Ala | Glu | Val | Ser | Asp | Pro | Lys | Tyr | Asp | Glu | Ser | Asp | Val | Pro | Ala |
|---|---|---|---|---|---|---|---|---|---|---|---|---|---|---|---|
| | | 35 | | | | | 40 | | | | | 45 | | | |

| Glu | Leu | Gln | Val | Leu | Lys | Glu | Pro | Leu | Gln | Gln | Pro | Ala | Phe | Pro | Phe |
|---|---|---|---|---|---|---|---|---|---|---|---|---|---|---|---|
| | 50 | | | | | 55 | | | | | 60 | | | | |

| Ala | Val | Ala | Asn | Gln | Leu | Leu | Leu | Val | Ser | Leu | Leu | Glu | His | Leu | Ser |
|---|---|---|---|---|---|---|---|---|---|---|---|---|---|---|---|
| 65 | | | | | 70 | | | | | 75 | | | | | 80 |

| His | Val | His | Glu | Pro | Asn | Pro | Leu | Arg | Ser | Arg | Gln | Val | Phe | Lys | Leu |
|---|---|---|---|---|---|---|---|---|---|---|---|---|---|---|---|
| | | | | 85 | | | | | 90 | | | | | 95 | |

| Leu | Cys | Gln | Thr | Phe | Ile | Lys | Met | Gly | Leu | Leu | Ser | Ser | Phe | Thr | Cys |
|---|---|---|---|---|---|---|---|---|---|---|---|---|---|---|---|
| | | | 100 | | | | | 105 | | | | | 110 | | |

| Ser | Asp | Glu | Phe | Ser | Ser | Leu | Arg | Leu | His | His | Asn | Arg | Ala | Ile | Thr |
|---|---|---|---|---|---|---|---|---|---|---|---|---|---|---|---|
| | | 115 | | | | | 120 | | | | | 125 | | | |

| His | Leu | Met | Arg | Ser | Ala | Arg | Glu | Arg | Val | Arg | Gln | Asp | Pro | Cys | Ala |
|---|---|---|---|---|---|---|---|---|---|---|---|---|---|---|---|
| | 130 | | | | | 135 | | | | | 140 | | | | |

| Asp | Asn | Ser | His | Ile | Gln | Lys | Ile | Arg | Ser | Arg | Glu | Val | Ala | Leu | Glu |
|---|---|---|---|---|---|---|---|---|---|---|---|---|---|---|---|
| 145 | | | | | 150 | | | | | 155 | | | | | 160 |

| Ala | Gln | Thr | Ser | Arg | Tyr | Leu | Asn | Glu | Phe | Glu | Glu | Leu | Ser | Ile | Leu |
|---|---|---|---|---|---|---|---|---|---|---|---|---|---|---|---|
| | | | | 165 | | | | | 170 | | | | | 175 | |

| Gly | Lys | Gly | Gly | Tyr | Gly | Arg | Val | Tyr | Lys | Val | Arg | Asn | Lys | Leu | Asp |
|---|---|---|---|---|---|---|---|---|---|---|---|---|---|---|---|
| | | | 180 | | | | | 185 | | | | | 190 | | |

| Gly | Gln | Tyr | Tyr | Ala | Ile | Lys | Lys | Ile | Leu | Ile | Lys | Gly | Ala | Thr | Lys |
|---|---|---|---|---|---|---|---|---|---|---|---|---|---|---|---|
| | | 195 | | | | | 200 | | | | | 205 | | | |

| Thr | Asp | Cys | Met | Lys | Val | Leu | Arg | Glu | Val | Lys | Val | Leu | Ala | Gly | Leu |
|---|---|---|---|---|---|---|---|---|---|---|---|---|---|---|---|
| | 210 | | | | | 215 | | | | | 220 | | | | |

| Gln | His | Pro | Asn | Ile | Val | Gly | Tyr | His | Thr | Ala | Trp | Ile | Glu | His | Val |
|---|---|---|---|---|---|---|---|---|---|---|---|---|---|---|---|
| 225 | | | | | 230 | | | | | 235 | | | | | 240 |

| His | Val | His | Val | Gln | Ala | Asp | Arg | Val | Pro | Ile | Gln | Leu | Pro | Ser | Leu |
|---|---|---|---|---|---|---|---|---|---|---|---|---|---|---|---|
| | | | | 245 | | | | | 250 | | | | | 255 | |

| Glu | Val | Leu | Ser | Asp | Gln | Glu | Glu | Asp | Arg | Asp | Gln | Tyr | Gly | Val | Lys |
|---|---|---|---|---|---|---|---|---|---|---|---|---|---|---|---|
| | | | 260 | | | | | 265 | | | | | 270 | | |

| Asn | Asp | Ala | Ser | Ser | Ser | Ser | Ser | Ile | Ile | Phe | Ala | Glu | Phe | Ser | Pro |
|---|---|---|---|---|---|---|---|---|---|---|---|---|---|---|---|
| | | 275 | | | | | 280 | | | | | 285 | | | |

| Glu | Lys | Glu | Lys | Ser | Ser | Asp | Glu | Cys | Ala | Val | Glu | Ser | Gln | Asn | Asn |
|---|---|---|---|---|---|---|---|---|---|---|---|---|---|---|---|
| | 290 | | | | | 295 | | | | | 300 | | | | |

| Lys | Leu | Val | Asn | Tyr | Thr | Thr | Asn | Leu | Val | Val | Arg | Asp | Thr | Gly | Glu |
|---|---|---|---|---|---|---|---|---|---|---|---|---|---|---|---|
| 305 | | | | | 310 | | | | | 315 | | | | | 320 |

| Phe | Glu | Ser | Ser | Thr | Glu | Arg | Gln | Glu | Asn | Gly | Ser | Ile | Val | Glu | Arg |
|---|---|---|---|---|---|---|---|---|---|---|---|---|---|---|---|
| | | | | 325 | | | | | 330 | | | | | 335 | |

| Gln | Leu | Leu | Phe | Gly | His | Asn | Ser | Asp | Val | Glu | Glu | Asp | Phe | Thr | Ser |
|---|---|---|---|---|---|---|---|---|---|---|---|---|---|---|---|
| | | | 340 | | | | | 345 | | | | | 350 | | |

| Ala | Glu | Glu | Ser | Ser | Glu | Glu | Asp | Leu | Ser | Ala | Leu | Arg | His | Thr | Glu |
|---|---|---|---|---|---|---|---|---|---|---|---|---|---|---|---|
| | | 355 | | | | | 360 | | | | | 365 | | | |

| Val | Gln | Tyr | His | Leu | Met | Leu | His | Ile | Gln | Met | Gln | Leu | Cys | Glu | Leu |
|---|---|---|---|---|---|---|---|---|---|---|---|---|---|---|---|
| | 370 | | | | | 375 | | | | | 380 | | | | |

| Ser | Leu | Trp | Asp | Trp | Ile | Ala | Glu | Arg | Asn | Arg | Ser | Arg | Glu | Cys |
|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
|Val|Asp|Glu|Ser|Ala|Cys|Pro|Tyr|Val|Met|Val|Ser|Val|Ala|Thr|Lys|
| | | | |405| | | |410| | | |415| | |
|Ile|Phe|Gln|Glu|Leu|Val|Glu|Gly|Val|Phe|Tyr|Ile|His|Asn|Met|Gly|
| | | |420| | | |425| | | |430| | | |
|Ile|Val|His|Arg|Asp|Leu|Lys|Pro|Arg|Asn|Ile|Phe|Leu|His|Gly|Pro|
| | |435| | | |440| | | |445| | | | |
|Asp|Gln|Gln|Val|Lys|Ile|Gly|Asp|Phe|Gly|Leu|Ala|Cys|Ala|Asp|Ile|
| |450| | | |455| | | |460| | | | | |
|Ile|Gln|Lys|Asn|Ala|Ala|Arg|Thr|Ser|Arg|Asn|Gly|Glu|Arg|Ala|Pro|
|465| | | |470| | | |475| | | | |480| | |
|Thr|His|Thr|Ser|Arg|Val|Gly|Thr|Cys|Leu|Tyr|Ala|Ser|Pro|Glu|Gln|
| | | |485| | | |490| | | | |495| | | |
|Leu|Glu|Gly|Ser|Glu|Tyr|Asp|Ala|Lys|Ser|Asp|Met|Tyr|Ser|Val|Gly|
| | |500| | | |505| | | |510| | | | |
|Val|Ile|Leu|Leu|Glu|Leu|Phe|Gln|Pro|Phe|Gly|Thr|Glu|Met|Glu|Arg|
| |515| | | |520| | | |525| | | | | |
|Ala|Glu|Val|Leu|Thr|Gly|Val|Arg|Ala|Gly|Arg|Ile|Pro|Asp|Ser|Leu|
|530| | | |535| | | |540| | | | | | |
|Ser|Lys|Arg|Cys|Pro|Ala|Gln|Ala|Lys|Tyr|Val|Gln|Leu|Leu|Thr|Arg|
|545| | | |550| | | |555| | | | |560| | |
|Arg|Asn|Ala|Ser|Gln|Arg|Pro|Ser|Ala|Leu|Gln|Leu|Leu|Gln|Ser|Glu|
| | | |565| | | |570| | | | |575| | | |
|Leu|Phe|Gln|Asn|Ser|Ala|His|Val|Asn|Leu|Thr|Leu|Gln|Met|Lys|Ile|
| | |580| | | |585| | | |590| | | | |
|Ile|Glu|Gln|Glu|Arg|Glu|Ile|Glu|Glu|Leu|Lys|Lys|Gln|Leu|Ser|Leu|
| |595| | | |600| | | |605| | | | | |
|Leu|Ser|Gln|Ala|Arg|Gly|Val|Arg|Ser|Asp|Arg|Arg|Asp|Gly|Glu|Leu|
|610| | | |615| | | |620| | | | | | |
|Pro|Ala| | | | | | | | | | | | | | |
|625| | | | | | | | | | | | | | | |

( 2 ) INFORMATION FOR SEQ ID NO:3:

( i ) SEQUENCE CHARACTERISTICS:
      ( A ) LENGTH: 76 amino acids
      ( B ) TYPE: amino acid
      ( C ) STRANDEDNESS: unknown
      ( D ) TOPOLOGY: unknown ( i i ) MOLECULE TYPE: peptide ( x i ) SEQUENCE DESCRIPTION: SEQ ID NO:3:

| | | | | | | | | | | | | | | |
|---|---|---|---|---|---|---|---|---|---|---|---|---|---|---|---|
|Thr|Glu|Glu|Tyr|Gln|Leu|Phe|Glu|Glu|Leu|Gly|Lys|Gly|Ala|Phe|Ser|
|1| | | |5| | | | |10| | | | |15| |
|Val|Val|Arg|Arg|Cys|Val|Lys|Val|Leu|Ala|Gly|Gln|Glu|Tyr|Ala|Ala|
| | | |20| | | | |25| | | | |30| | |
|Lys|Ile|Ile|Asn|Thr|Lys|Lys|Leu|Ser|Ala|Arg|Lys|His|Gln|Lys|Leu|
| | |35| | | | |40| | | | |45| | | |
|Glu|Arg|Glu|Ala|Arg|Ile|Cys|Arg|Leu|Leu|Lys|His|Pro|Asn|Ile|Val|
| |50| | | | |55| | | | |60| | | | |
|Arg|Leu|His|Asp|Ser|Ile|Ser|Glu|Glu|Gly|His|His| | | | |
|65| | | | |70| | | | |75| | | | | | |

( 2 ) INFORMATION FOR SEQ ID NO:4:

( i ) SEQUENCE CHARACTERISTICS:
      ( A ) LENGTH: 26 amino acids
      ( B ) TYPE: amino acid (C) STRANDEDNESS: unknown
(D) TOPOLOGY: unknown (ii) MOLECULE TYPE: peptide (xi) SEQUENCE DESCRIPTION: SEQ ID NO:4:

```
Tyr Leu Ile Phe Asp Leu Val Thr Gly Gly Glu Leu Phe Glu Asp Ile
  1               5                  10                  15
Val Ala Arg Glu Tyr Tyr Ser Glu Ala Asp
             20                  25
```

(2) INFORMATION FOR SEQ ID NO:5:

(i) SEQUENCE CHARACTERISTICS:
        (A) LENGTH: 59 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:5:

```
Ala Ser His Cys Ile Gln Gln Ile Leu Glu Ala Val Leu His Cys His
  1               5                  10                  15
Gln Met Gly Val Val His Arg Asp Leu Lys Pro Glu Asn Ile Leu Leu
             20                  25                  30
Ala Ser Lys Leu Lys Gly Ala Ala Val Lys Leu Ala Asp Phe Gly Leu
         35                  40                  45
Ala Ile Glu Val Glu Gly Glu Gln Gln Ala Trp
     50                  55
```

(2) INFORMATION FOR SEQ ID NO:6:

(i) SEQUENCE CHARACTERISTICS:
        (A) LENGTH: 69 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:6:

```
Phe Gly Phe Ala Gly Thr Pro Gly Tyr Leu Ser Pro Glu Val Leu Arg
  1               5                  10                  15
Lys Asp Pro Tyr Gly Lys Pro Val Asp Leu Trp Trp Cys Gly Val Ile
             20                  25                  30
Leu Tyr Ile Leu Leu Val Gly Tyr Pro Pro Phe Trp Asp Glu Asp Gln
         35                  40                  45
His Arg Leu Tyr Gln Gln Ile Lys Ala Gly Ala Tyr Asp Phe Pro Ser
     50                  55                  60
Pro Glu Trp Asp Thr
 65
```

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

```
Val Thr Pro Glu Ala Lys Asp Leu Leu Asn Lys Met Leu Thr Ile Asn
```

```
            1               5                    10                        15
```

Pro Ser Lys Arg Ile Thr Ala Ala Glu Ala Leu Lys His
                20                  25

(2) INFORMATION FOR SEQ ID NO:8:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

His Glu Asp Val Ser Leu Gly Glu Leu Leu Gly Lys Gly Asn Phe Gly
1               5                    10                        15

Glu Val Tyr Lys Gly Thr Leu Lys Asp Lys Thr Pro
                20                  25

(2) INFORMATION FOR SEQ ID NO:9:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:9:

Ala Val Lys Thr Cys Lys Glu Asp Leu Pro
1               5                    10

(2) INFORMATION FOR SEQ ID NO:10:

(i) SEQUENCE CHARACTERISTICS:
        (A) LENGTH: 35 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:10:

Gln Glu Leu Lys Ile Lys Phe Leu Gln Glu Ala Lys Ile Leu Lys Gln
1               5                    10                        15

Tyr Asp His Pro Asn Leu Val Lys Leu Ile Gly Val Cys Thr Gln Arg
                20                  25                        30

Gln Pro Val
        35

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:11:

Tyr Ile Ile Met Glu Leu Val Pro Gly Gly Asp Phe Leu Ser Phe Leu
1               5                    10                        15

Arg Lys Arg Lys Asp Glu Leu Lys Leu Lys Gln
                20                  25

( 2 ) INFORMATION FOR SEQ ID NO:12:

( i ) SEQUENCE CHARACTERISTICS:
        ( A ) LENGTH: 37 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Leu  Val  Arg  Phe  Ser  Leu  Asp  Val  Ala  Ala  Gly  Met  Leu  Tyr  Leu  Glu
1                   5                        10                       15

Gly  Lys  Asn  Cys  Ile  His  Arg  Asp  Leu  Ala  Ala  Arg  Asn  Cys  Leu  Val
               20                       25                       30

Gly  Glu  Asn  Asn  Thr
               35
```

( 2 ) INFORMATION FOR SEQ ID NO:13:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Leu  Lys  Ile  Ser  Asp  Phe  Gly  Met  Ser  Arg  Gln  Glu  Asp  Gly  Gly  Val
1                   5                        10                       15

Tyr  Ser  Ser  Ser
               20
```

( 2 ) INFORMATION FOR SEQ ID NO:14:

( i ) SEQUENCE CHARACTERISTICS:
        ( A ) LENGTH: 67 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

```
Gly  Leu  Lys  Gln  Ile  Pro  Ile  Lys  Trp  Thr  Ala  Pro  Phe  Ala  Leu  Asn
1                   5                        10                       15

Tyr  Gly  Arg  Tyr  Ser  Ser  Glu  Ser  Asp  Val  Trp  Ser  Phe  Gly  Ile  Leu
               20                       25                       30

Leu  Trp  Glu  Thr  Phe  Ser  Leu  Gly  Val  Cys  Pro  Tyr  Pro  Gly  Met  Thr
               35                       40                       45

Asn  Gln  Gln  Ala  Arg  Glu  Gln  Val  Glu  Arg  Gly  Tyr  Arg  Met  Ser  Ala
          50                       55                       60

Pro  Gln  Asn
65
```

( 2 ) INFORMATION FOR SEQ ID NO:15:

( i ) SEQUENCE CHARACTERISTICS:
        ( A ) LENGTH: 29 amino acids
        ( B ) TYPE: amino acid
        ( C ) STRANDEDNESS: unknown
        ( D ) TOPOLOGY: unknown ( i i ) MOLECULE TYPE: peptide (x i) SEQUENCE DESCRIPTION: SEQ ID NO:15:

```
Cys Pro Glu Glu Ile Phe Thr Ile Met Met Lys Cys Trp Asp Tyr Lys
1                 5               10                      15

Pro Glu Asn Arg Pro Lys Phe Ser Asp Leu His Lys Glu
                20              25
```

DNA ENCODING THE HEME-REGULATED EUKARYOTIC INITIATION FACTOR 2α KINASE

This is a divisional of U.S. Ser. No. 07/938,782 U.S. Pat. No. 5,525,513 entitled "DNA Encoding the Heme-Regulated Eukaryotic Initiation Factor 2α Kinase" filed on Aug. 31, 1992, now U.S. Pat. No. 5,525,513, by Jane-Jane Chen and Irving M. London.

The United States government has certain rights in this invention by virtue of government support under Grant Number DMB-8903581 awarded by the National Science Foundation and NIH-5R01DK16272-19 awarded by the National Institutes of Health. The United States government has rights in this invention by virtue of grants from the National Institutes of Health, DK 16272 and GM 42504 and from the National Science Foundation, DMB-890538.

BACKGROUND OF THE INVENTION

The United States government has rights in this invention by virtue of grants from the National Institutes of Health, DK 16272 and GM 42504 and from the National Science Foundation, DMB-890538.

This application claims priority to Japanese patent application No. 4-81664 filed Mar. 2, 1992.

The present invention is an isolated nucleic acid sequence encoding the heme-regulated eukaryotic initiation factor 2α kinase, and methods of use thereof in inhibition of cellular proliferation.

Heme controls the synthesis of protein in reticulocytes. In heme-deficiency, there is diminished initiation of protein synthesis with disaggregation of polyribosomes. The principal mechanism of the inhibition of initiation of protein synthesis is the phosphorylation of the α-subunit of the eukaryotic initiation factor 2, eIF-2α. In addition to heme-deficiency, oxidized glutathione (GSSG) and low levels of double stranded RNA inhibit initiation by promoting phosphorylation of eIF-2α.

The translation of mRNA in eukaryotic cells occurs in the cytoplasm. In the first step of initiation, free 80 S ribosomes are in equilibrium with their 40 S and 60 S subunits. In the presence of eIF-3, 40 S subunits bind the eIF-3 and eIF-4C to form a 43 S ribosomal complex; the binding of eIF-3 and eIF-4C to the 40 S subunit inhibits the joining of the 60 S subunit.

In the next step, eIF-2 binds GTP and the initiator tRNA, Met-tRNA$_f$, in a ternary complex. The binding by eIF-2 is specific for both guanine nucleotides and for Met-tRNA$_f$. The ternary complex now binds to the 43 S ribosomal complex to form the 43 S preinitiation complex. The 43 S preinitiation complex binds mRNA in an ATP-dependent reaction in which eIF-4A, eIF-4B, and eIF-4F form a complex with the mRNA. The product of the binding of mRNA to the 43 S structure is bound close to the ribosome and the AUG initiator codon is downstream from the cap structure.

The joining of the 48 S preinitiation complex and the 60 S subunit is catalyzed by eIF-5 which has a ribosome-dependent GTPase activity. The joining reaction is accompanied by the release of the initiation factors eIF-3 and eIF-4C, eIF-2 is translocated to 60 S subunit as a binary complex, eIF2-GDP. The product of the joining reaction is the 80 S initiation complex. Formation of the active 80 S initiation complex is the final step in initiation. The Met-tRNA$_f$ is positioned in the P (peptidyl) site on the ribosome for the start of polypeptide elongation.

The sequence of steps in the process of initiation affords several opportunities for regulation. These include the recycling of eIF-2 after its release as the eIF-2-GDP complex; the formation of the ternary complex; and the relative affinities of mRNAs for eIF-2 and for eIF-4A, -4B, and -4F in determining the relative rates of translation of the mRNAs.

A schematic summary of eukaryotic initiation is shown in FIG. 1. Heme-deficiency inhibited initiation of protein synthesis is characterized by a brief period of control linear synthesis, followed by an abrupt decline in this rate and by disaggregation of polyribosomes, associated with a decrease in the formation of the eIF-2-Met-tRNA$_f$-GTP ternary complex and the 40 S-eIF-2Met-tRNA$_f$-GTP 43 S initiation complex. The fundamental mechanism for the inhibition is the activation of cAMP independent protein kinases that specifically phosphorylate the 38-kDa α-subunit of eIF-2 (eIF-2α). Dephosphorylation of eIF-2α accompanies the recovery of protein synthesis upon addition of hemin to inhibited heme-deficient lysates.

The heme-regulated eukaryotic initiation factor 2α (eIF-2α) kinase, also called heme-regulated inhibitor (HRI), plays a major role in this process. HRI is a cAMP-independent protein kinase that specifically phosphorylates the α subunit (eIF-2α) of the eukaryotic initiation factor 2 (eIF-2). Phosphorylation of eIF-2α in reticulocyte lysates results in the binding and sequestration of reversing factor RF, also designated as guanine nucleotide exchange factor or eIF-2B, in a RF-eIF-2 (αP) complex; the unavailability of RF, which is required for the exchange of GTP for GDP in the recycling of eIF-2 and in the formation of the eIF-2-Met-tRNA$_f$-GTP ternary complex, resulting in the cessation of the initiation of protein synthesis.

Although the mechanism of regulation of protein synthesis by HRI has been extensively studied, little is known about the structure and regulation of HRI itself. Chen, J. -J., et al., *Proc. Natl. Acad. Sci.*, USA 88:315–319 (1991) previously reported the amino acid sequences of three tryptic peptides of heme-reversible HRI. HRI peptide P-52 contains the sequence Asp-Phe-Gly, which is the most highly conserved short stretch in conserved domain VII of protein kinases as presented by Hanks, Quinn, and Hunter, *Science* 241:42–52 (1988). The N-terminal 14 amino acids of HRI peptide P-74 show 50–60% identity to the conserved domain IX of kinase-related transforming proteins. These findings are consistent with the autokinase and eIF-2α kinase activities of HRI. As reported by Pal et al., *Biochem.* 30:2555–2562 (1991), this protein appears to be erythroid-specific and antigenically different in different species.

In view of the activity and relationships of HRI to other protein kinases involved in cellular transformation, it would be advantageous to have the nucleic acid sequence encoding HRI. However, since the gene is only expressed during a very limited time period, i.e., during erythroid differentiation, and in an extremely minuscule amount, this was not a simple process. Moreover, even though three peptides isolated by tryptic digest had been sequenced, it was not clear if these were from HRI or from a contaminant of the HRI preparation. Obtaining a library containing a full length HRI cDNA is also difficult.

It is therefore an object of the present invention to provide a cDNA sequence encoding HRI.

It is a further object of the present invention to provide methods for expression of HRI in mammalian cells.

It is still another object of the present invention to provide methods of use of the isolated DNA sequence encoding HRI to inhibit cell proliferation, by inhibiting protein synthesis, especially of transformed cells and in diseases such as psoriasis.

It is another object of the present invention to provide methods of use of the sequence encoding HRI and dsI to induce cellular differentiation and treat cancers involving arrested differentiation.

SUMMARY OF THE INVENTION

The cDNA which encodes heme-regulated eIF-2α kinase (HRI) has been cloned from a lambda Zap II cDNA library of rabbit reticulocytes. The rabbit HRI cDNA is highly homologous to human HRI and hybridizes to the human HRI DNA under moderately stringent conditions. The rabbit HRI cDNA contains 2729 nucleotides and encodes 626 amino acids. In vitro translation of HRI mRNA transcribed from HRI cDNA yields a 90 kDa polypeptide with eIF-2α kinase activity. This 90 kDa polypeptide is recognized by an anti-HRI non-species specific monoclonal antibody. These properties are characteristic of authentic HRI.

Since HRI is a potent inhibitor of protein synthesis, it is anti-proliferative in nature. In addition, the unusually high degree of homology of HRI to three protein kinases involved in the regulation of cell division suggests that HRI may play a direct role in the regulation of cell division. The availability of HRI cDNA provides a means to study the regulation and the structure and function relationship of HRI. Furthermore, since regulation of protein synthesis is vital for cell growth and differentiation, the cDNA can be inserted into cells to manipulate proliferation and differentiation, especially of cells that are proliferating in an uncontrolled manner or characterized by arrested differentiation, such as some of the types of cancers.

Initiation of protein synthesis can also be regulated by another eIF-2α kinase which is activated by double-stranded RNA (dsI). Both HRI and dsI phosphorylate eIF-2α at the same site. However, dsI is induced by interferon and represents an interferon mediated response to viral infection. Since HRI and dsI are eIF-2α kinases, they are both anti-viral in nature, but mechanisms of inactivating dsi by viruses should not affect HRI activity. Therefore, when introduced into the proper target, HRI should be as potent or more potent than dsI in its anti-viral action.

Deletion mutants of HRI cDNA can be constructed that are insensitive to regulation by heme. This heme-insensitive HRI should be more effective than native HRI in its anti-viral and anti-proliferative action.

BRIEF DESCRIPTION OF THE DRAWINGS

FIG. 3 is an alignment of the conserved catalytic domains of HRI (residues 167–275, 414–551, and 578–606 of Sequence ID No. 2) with other protein kinases. The portions of CaMPK are divided by one or more dots indicating breaks in the conserved sequence. A sequence identification number has been assigned to each portion, respectively. Accordingly, the amino acid sequences of CaMPK set forth in FIG. 3 are Sequence ID No. 3, Sequence ID No. 4, Sequence ID No. 5, Sequence ID No. 6, and Sequence ID No. 7; and the amino acid sequences of Src set forth in FIG. 3 are Sequence ID No. 8, Sequence ID No. 9, Sequence ID No. 10, Sequence ID No. 11, Sequence ID No. 12, Sequence ID No. 13, Sequence ID No. 14, and Sequence ID No. 15. The conserved catalytic domains are indicated by the Roman numerals (I to XI). The conserved invariant amino acid residues are shown as black boxes with white letters in italicized letters. The semi-conserved amino acid residues of similar structure are shown in bolded letters. Small gaps are shown by dots ( . . . . ). There is an insertion of 138 amino acids in HRI between domains V and VI as indicated by {138}. There is an insertion of 26 amino acids in HRI between domains X and XI as indicated by {26}. The additional amino acids beyond the conserved domains are indicated by the numbers on both N- and C- termini. Single letter code of amino acids is used.

DETAILED DESCRIPTION OF THE INVENTION

Figure 1:
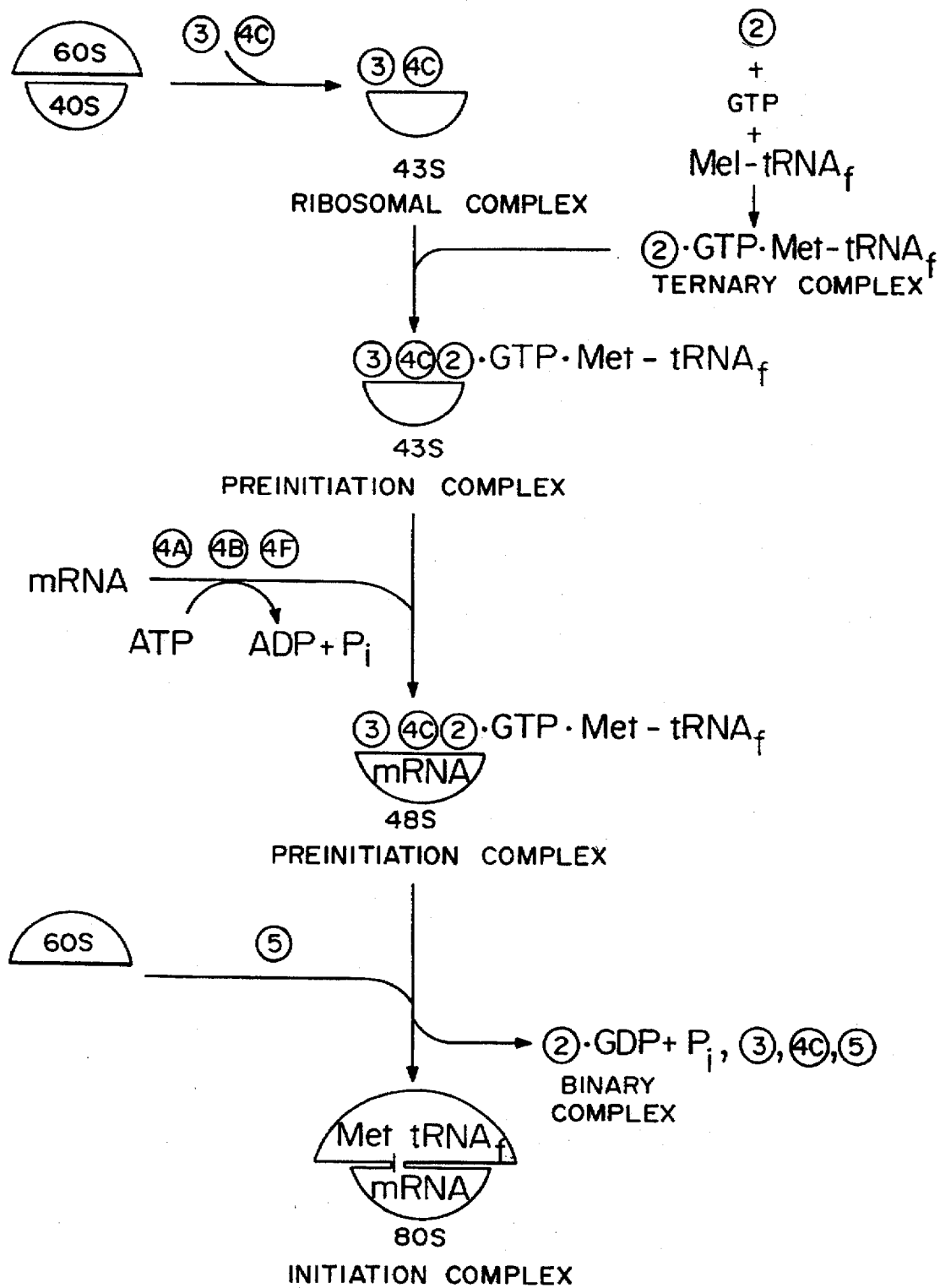
FIG. 1 is a schematic of eukaryotic initiation of protein synthesis. Numbers in circles refer to eukaryotic initiation factors.
Figure 2:
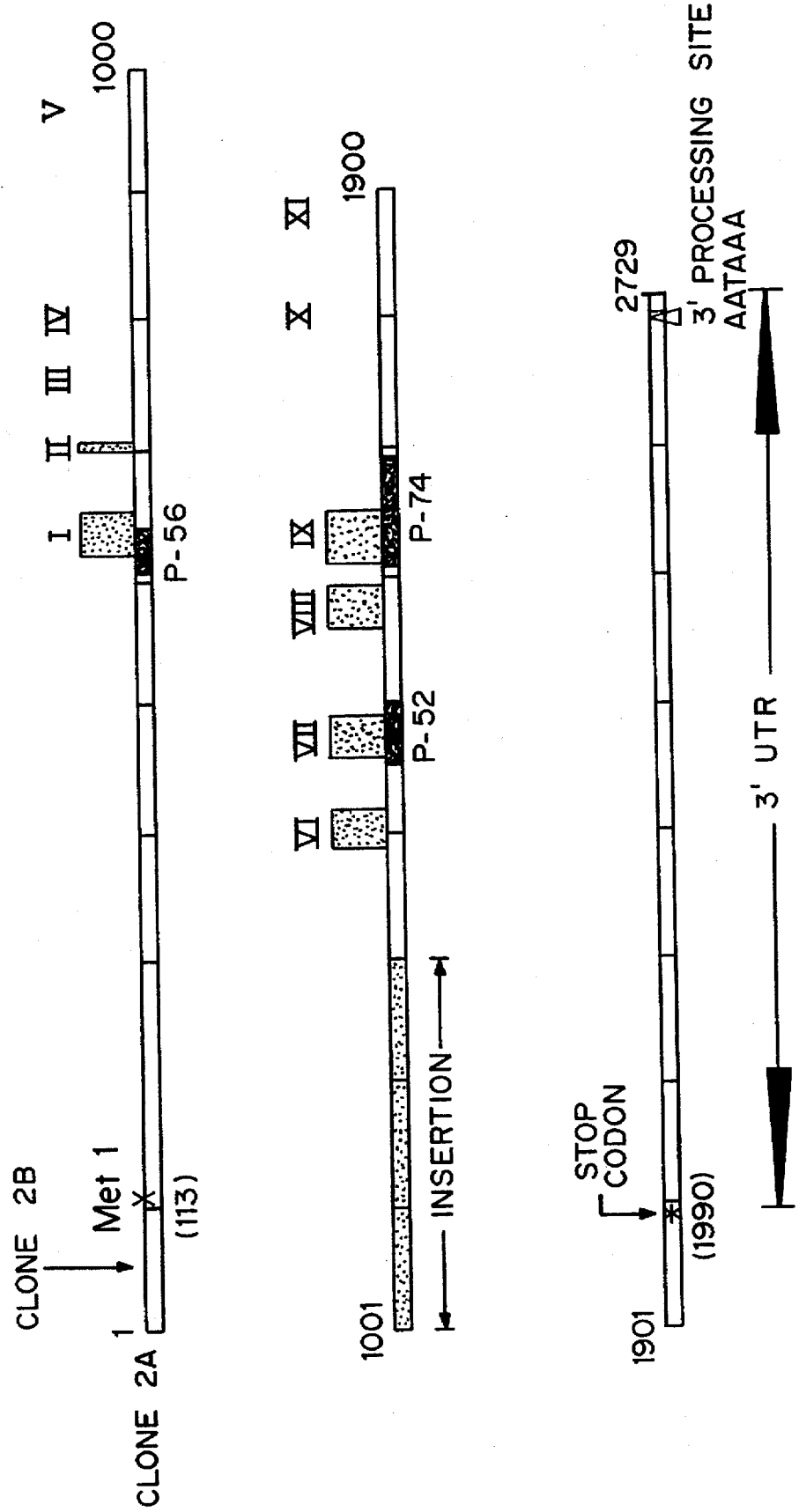
FIG. 2 is a schematic of HRI cDNA indicating the locations of the eleven domains, the HRI specific insertion region, and the three peptides previously sequenced and identified as unique to HRI: P-52, corresponding to amino acids 454 to 467, containing Asp-Phe-Gly, which is the most highly conserved short stretch in catalytic domain VII of protein kinases; P-74, corresponding to amino acids 506 to 525, containing the conserved amino acid residues Asp-(Met)-Tyr-Ser-(Val)-Gly-Val found in catalytic domain IX of protein kinases, and P-56, corresponding to amino acids 166–178.

HRI cDNA was cloned from a lambda Zap II cDNA library of rabbit reticulocytes. As described in more detail below, this cDNA is highly homologous to human DNA encoding HRI and has been used to obtain a clone encoding the human HRI, as well as HRI from other species such as mouse (although there appears to be slightly greater homology between rabbit and human than between rabbit and mouse HRI). The rabbit HRI cDNA contains 2729 nucleotides and encodes 626 amino acids. The nucleic acid sequence has been deposited in the Gene Bank data base (accession No. M69035). In vitro translation of HRI mRNA transcribed from HRI cDNA yields a 90 kDa polypeptide with eIF-2α kinase activity. This 90 kDa polypeptide is recognized by anti-HRI monoclonal antibody. These properties are characteristic of authentic HRI.

The open reading frame sequence of the HRI cDNA contains all eleven catalytic domains of protein kinases with consensus sequences of serine/threonine protein kinases in conserved catalytic domains VI and VIII. The HRI cDNA also contains an insert of approximately 140 amino acids between catalytic domains V and VI. The HRI cDNA coding sequence has extensive homology to GCN2 protein kinase of *S. cerevisiae* and to human double stranded RNA-dependent eIF-2α kinase. It therefore is believed that GCN2 protein kinase may be an eIF-2α kinase in yeast. Recently, it has been shown that phosphorylation of e2F-2α by GCN2 is required for the translational control of yeast GCN4, Dever, et al., *Cell* 28, 585–596 (1992).In addition, HRI has an unusually high degree of homology to three protein kinases, NimA, Weeland CDC2, which are involved in the regulation of the cell cycle.

Isolation and sequencing of cDNA encoding HRI from rabbit reticulocytes.

PCR Amplification of HRI cDNA between P-52 and P-74.

Poly $A^+$ mRNA (1 µg) was reverse-transcribed to obtain single stranded cDNAs according to the method of Frohman, M. A., Dush, M. V. and Martin, G. R., (1988) *Proc. Natl. Acad. Sci. USA*, 85, 8998–9002. The sense-strand oligo-deoxynucleotide of P-52 and the antisense-strand oligo-deoxynucleotide of P-74, deduced with preferred codon usage as in Lathe, R., (1985) J. Mol. Biol., 183, 1–12, were used as primers. The PCR reactions were carried out in the presence of single stranded cDNA template and each primer (1 µM) for 40 cycles (94° C. ×1 min, 47° C.×2 min and 72° C.×3 min).

Preparation of lambda Zap II cDNA library of rabbit reticulocytes and the isolation of HRI cDNA clones.

cDNAs of rabbit reticulocytes were prepared using Pharmacia's cDNA synthesis kit. The cDNAs larger than 500 bp were pooled and were ligated to lambda Zap II vector (Stratagene). The cDNA library obtained has 95% recombinant efficiency. The cDNA library was hybridized at 42° C. overnight in a solution containing 5× Denhardt's solution, 6× SSPE, salmon sperm DNA (500 mg/ml), tRNA (1.7 mg/ml), 0.4% SDS plus heat-denatured nick-translated [$^{32}$P] -HRI cDNA probe ($10^6$ cpm/ml). (1× SSPE=0.18M NaCl/10 mM Na phosphate/1 mM EDTA pH 7.4; 1× Denhardt's solution=0.02% polyvinylpyrrolidone/0.02% Ficoll/0.02% BSA). The nitrocellulose was then washed three times with 6× SSPE and 0.1% SDS at room temperature for 5 minutes each, followed by washing twice at 50° C. under the same salt conditions for 10 minutes each. HRI cDNA was subcloned into pBlue Script plasmid by in vivo excision from the recombinant lambda Zap II as described by Stratagene. The DNA sequence of HRI cDNA was determined by the method of dideoxynucleotide chain termination of Sanger, et al., *Proc. Natl. Acad. Sci.*, USA, 74:5463–5467 (1977) with the modification described by Fawcett and Barlett, *BioTechniques*, 9:46–48 (1990).

It was not possible to use P-52, P-56, or P-74 alone to screen the library. In fact, only one of the oligonucleotides derived from these peptides worked in a Northern blot. It was necessary to combine two of the peptides in one of the many possible orientations in order to develop a probe that was useful in pulling out a full length clone.

The homology of the amino acid sequences of HRI tryptic peptides P-52 and P-74 to the conserved domains VII and IX of protein kinases made it possible to predict that P-52 was positioned to the N-terminal side of P-74. This information was used to design primers for PCR amplification of a partial HRI cDNA. Using these two primers, two amplified cDNA fragments which were approximately 230 bp in length were obtained.

This cDNA fragment was subcloned and sequenced. Excluding the 15 bp EcoR1 restriction sites present on both primers, the remaining 219 bp sequence encodes an open reading frame for 73 amino acids. The newly obtained 38 amino acid sequence of HRI deduced from this cDNA sequence contains the consensus sequence (Gly-Thr/Ser-X-X-Tyr/Phe-X-Ala/Ser-Pro-Glu) of serine/threonine protein kinases located in the conserved domain VIII. This observation is consistent with the finding by Pathak, et al., *Mol. Cell. Biol.*, 8:993–995 (1988), that HRI phosphorylates eIF-2α at serine -51. Furthermore, the amino acid sequences of HRI between conserved domains VII, VIII, and IX are unique to HRI.

150,000 recombinant clones were screened with the 234 bp probe of HRI. Among the 12 positive clones of the primary screen, five were full-length and contain a cDNA insert of approximately 2700 bp. The 2729 nucleotide sequence of HRI cDNA is shown below. There are 112 nucleotides preceding the first ATG. Starting from this first ATG (nt 113), the open reading frame continues to nucleotide 1990 encoding 626 amino acids followed by multiple stop codons in the 3' untranslated region of 739 nucleotides. It should be noted that the first 250 nt of HRI cDNA are very rich in GC content (80%). The nucleotide sequence of this area of HRI cDNA was finally obtained by using terminal deoxytransferase and pyrophosphatase. The overlapping repeat of the AATAAA polyadenylation signal is found at nucleotides 2689–2698, 11 nucleotides from the poly A tail. The deduced amino acid sequence of the HRI cDNA contains the exact amino acid sequences of the three tryptic peptides of HRI previously obtained by microsequencing. P-52 is located in domain VII, P-56 in domain I, and P-74 in domain IX.

The deoxynucleotide sequence (PatentIn sequence No. 1) and deduced amino acid sequence (PatentIn sequence No. 2) of HRI cDNA are shown below. The numbers to the left indicate the position of nucleotides while the numbers to the right indicate the position of amino acids. An asterisk (*) indicates the first stop codon. Portions of deduced amino acid sequences which match exactly the amino acid sequences of HRI tryptic peptides (P-52, P-56 and P-74) are underlined and indicated. The overlapping and repeated polyadenylation signal sequence in the 3'-UTR, AATAAA is underlined.

```
  1                                            CGCACGGCGC
 11 TCGCGACCCGGACGCGCGAGGAGGCGGTCCCGGAGTCGGGGAGCTGGCGGG
 62 TGGGCTGTGGTCCCCGCATTTGCGCGCGCGGGCGCCCGCGCGTGACCGGCG
113 ATGCTGGGGGGCAGCGCCGGGACCCGCGGGGGCGAAGCCGAGGGCGACGGG
    MetLeuGlyGlySerAlaGlyThrArgGlyGlyGluAlaGluGlyAspGly       17
164 GCGGGGGCGGTGGGGGCGGTGGCCCCGCCGCCCGCCATCGACTTCCCCGCT
    AlaGlyAlaValGlyAlaValAlaProProProAlaIleAspPheProAla       34
215 GAGGTGTCGGATCCAAGTATGACGAGTCGGATGTCCCGGCAGAGCTGCAG
```

-continued

|  |  |
|---|---|
| GluValSerAspProLysTyrAspGluSerAspValProAlaGluLeuGln | 51 |
| 266 GTGCTGAAGGAGCCGCTGCAGCAGCCAGCCTTCCCCTTCGCCGTCGCCAAC<br>ValLeuLysGluProLeuGlnGlnProAlaPheProPheAlaValAlaAsn | 68 |
| 317 CAGCTGCTGCTCGTCTCCCTGCTGGAGCACCTGAGTCATGTGCACGAGCCA<br>GlnLeuLeuLeuValSerLeuLeuGluHisLeuSerHisValHisGluPro | 85 |
| 368 AACCCGCTTCGCTCCAGACAGGTGTTTAAACTGCTCTGTCAGACCTTCATC<br>AsnProLeuArgSerArgGlnValPheLysLeuLeuCysGlnThrPheIle | 102 |
| 419 AAAATGGGGCTGCTGTCTTCCTTCACCTGCAGCGACGAGTTTAGCTCATTG<br>LysMetGlyLeuLeuSerSerPheThrCysSerAspGluPheSerSerLeu | 119 |
| 470 AGGCTGCATCACAACAGAGCTATTACGCATCTGATGAGGTCCGCCAGAGAG<br>ArgLeuHisHisAsnArgAlaIleThrHisLeuMetArgSerAlaArgGlu | 136 |
| 521 AGAGTTCGGCAGGATCCCTGTGCTGATAATTCTCATATCCAGAAAATCAGG<br>ArgValArgGlnAspProCysAlaAspAsnSerHisIleGlnLysIleArg | 153 |
| 572 TCGCGAGAAGTTGCCTTGGAAGCACAGACCTCACGATACTTGAATGAGTTT<br>SerArgGluValAlaLeuGluAlaGlnThrSerArgTyrLeuAsnGluPhe | 170 |
| 623 GAAGAGCTCTCCATCCTGGGGAAAGGTGGCTATGGCCGAGTGTACAAGGTC<br>GluGluLeuSerIleLeuGlyLysGlyGlyTyrGlyArgValTyrLysVal | 187 |
| 674 AGGAATAAATTAGATGGCCAGTATTATGCAATTAAAAAAATTCTGATTAAA<br>ArgAsnLysLeuAspGlyGlnTyrTyrAlaIleLysLysIleLeuIleLys | 204 |
| 725 GGTGCAACTAAAACAGATTGCATGAAGGTATTACGAGAAGTGAAAGTGCTG<br>GlyAlaThrLysThrAspCysMetLysValLeuArgGluValLysValLeu | 221 |
| 776 GCGGGCCTCCAGCACCCTAATATCGTAGGCTATCACACCGCGTGGATAGAG<br>AlaGlyLeuGlnHisProAsnIleValGlyTyrHisThrAlaTrpIleGlu | 238 |
| 827 CATGTCCACGTTCACGTTCAAGCAGACAGAGTTCCGATTCAGTTGCCTTCT<br>HisValHisValHisValGlnAlaAspArgValProIleGlnLeuProSer | 255 |
| 878 CTGGAAGTGCTCTCTGACCAGGAAGAAGACAGAGATCAATATGGTGTTAAA<br>LeuGluValLeuSerAspGlnGluGluAspArgAspGlnTyrGlyValLys | 272 |
| 929 AATGATGCAAGCAGCAGCTCATCCATTATTTTCGCTGAGTTCTCCCCAGAA<br>AsnAspAlaSerSerSerSerIleIlePheAlaGluPheSerProGlu | 289 |
| 980 AAAGAAAAATCCTCTGACGAATGTGCCGTTGAGAGTCAGAATAACAAACTG<br>LysGluLysSerSerAspGluCysAlaValGluSerGlnAsnAsnLysLeu | 306 |
| 1031 GTGAACTACACCACCAACTTAGTGGTGAGGGACACCGGTGAGTTTGAATCG<br>ValAsnTyrThrThrAsnLeuValValArgAspThrGlyGluPheGluSer | 323 |
| 1082 TCCACGGAGCGCCAAGAGAACGGCTCGATCGTGGAGCGTCAGCTACTGTTC<br>SerThrGluArgGlnGluAsnGlySerIleValGluArgGlnLeuLeuPhe | 340 |
| 1133 GGGCATAACTCAGACGTAGAAGAGGATTTCACGTCCGCGGAGGAATCTTCT<br>GlyHisAsnSerAspValGluGluAspPheThrSerAlaGluGluSerSer | 357 |
| 1184 GAGGAAGACTTAAGCGCGTTGCGGCACACAGAGGTGCAGTACCACCTGATG<br>GluGluAspLeuSerAlaLeuArgHisThrGluValGlnTyrHisLeuMet | 374 |
| 1235 CTGCATATCCAGATGCAGCTGTGCGAGCTGTCCCTGTGGGACTGGATCGCC<br>LeuHisIleGlnMetGlnLeuCysGluLeuSerLeuTrpAspTrpIleAla | 391 |
| 1286 GAGAGGAACAGGCGGAGCCGAGAGTGCGTGGACGAATCTGCCTGTCCTTAT<br>GluArgAsnArgArgSerArgGluCysValAspGluSerAlaCysProTyr | 408 |
| 1337 GTTATGGTCAGTGTTGCAACAAAAATTTTTCAAGAACTGGTGGAAGGTGTG<br>ValMetValSerValAlaThrLysIlePheGlnGluLeuValGluGlyVal | 425 |
| 1388 TTTTACATACATAACATGGGCATCGTGCACAGAGACCTGAAGCCTAGAAAT<br>PheTyrIleHisAsnMetGlyIleValHisArgAspLeuLysProArgAsn | 442 |
| 1439 ATTTTTCTTCATGGTCCTGATCAACAAGTGAAAATAGGAGACTTTGGTCTG<br>IlePheLeuHisGlyProAspGlnGlnValLysIleGlyAspPheGlyLeu | 459 |
| 1490 GCCTGCGCCGACATCATCCAGAAGAATGCGGCCCGGACCAGCAGAAACGGG<br>AlaCysAlaAspIleIleGlnLysAsnAlaAlaArgThrSerArgAsnGly | 476 |
| 1541 GAGAGAGCACCCACACACACTTCCCGAGTGGGCACCTGTCTGTACGCCTCG<br>GluArgAlaProThrHisThrSerArgValGlyThrCysLeuTyrAlaSer | 493 |

-continued

```
1592 CCCGAGCAGTTGGAAGGATCGGAGTATGATGCCAAGTCAGACATGTACAGC
     ProGluGlnLeuGluGlySerGluTyrAspAlaLysSerAspMetTyrSer                510

1643 GTCGGCGTGATCCTGCTGGAGCTCTTCCAGCCCTTCGGGACAGAGATGGAG
     ValGlyValIleLeuLeuGluLeuPheGlnProPheGlyThrGluMetGlu                527

1694 CGGGCAGAGGTCCTGACGGGCGTGCGAGCTGGCCGCATACCCGACTCCCTC
     ArgAlaGluValLeuThrGlyValArgAlaGlyArgIleProAspSerLeu                544

1745 AGTAAGAGGTGCCCGGCGCAGGCCAAGTACGTCCAGCTGCTGACCAGGAGG
     SerLysArgCysProAlaGlnAlaLysTyrValGlnLeuLeuThrArgArg                561

1796 AACGCGTCCCAGCGGCCGTCCGCCCTTCAGCTGCTGCAGAGTGAGCTCTTC
     AsnAlaSerGlnArgProSerAlaLeuGlnLeuLeuGlnSerGluLeuPhe                578

1847 CAGAACTCCGCGCATGTTAACCTCACCCTACAGATGAAGATAATAGAGCAG
     GlnAsnSerAlaHisValAsnLeuThrLeuGlnMetLysIleIleGluGln                595

1898 GAAAGAGAAATCGAGGAACTCAAGAAGCAGCTGAGCCTCCTCTCCCAGGCC
     GluArgGluIleGluGluLeuLysLysLysGlnLeuSerLeuLeuSerGlnAla             612
                                                                ***

1949 CGAGGGGTGAGGAGTGACAGGCGAGACGGAGAGCTCCCTGCCTAGCCGTCA
     ArgGlyValArgSerAspArgArgAspGlyLeuProAla                            626

2000 CTCGGCCACGTCACAGGGGAACGTGGACTTGCACTTGCAGCAGTCAACTGG

2051 AATGGACAATTTCAAGCCTCCTGAGGTTCAGGCGGCATAATCCTCATTGG

2102 AATCACTCAGCCCGCATGACTCTCCCCTCATGCTGCTCTTCCCGGAGGTAC

2153 CTCCTGGTGACCTCCTGGTGACTGCTCCCAATTAAACTTACGCTTTTCCCT

2204 TTCCTATTCCGCAAGTCCCATTCCTGAGCCTCCTACCTAAGCATTAACTAA

2255 ATCTTAGGTATCGGTCTCCATTCTTTCTCCTTTGAATCCTGGCCACCTCGC

2306 TCCTTTAGAAGCACACTCACTGCCCCGCCACCACCCAAGGCCAGGCCTGCA

2357 CCCTGGCGCAACAGCTGCCAGTCTTAGTCCTTAGCTGCTGCTGCTGTTGCC

2408 AGAGACACCTGCTCCGTTCACTCCCTCCAGGGTGGAAGCTCAGCCTGTGAG

2459 CAGCGCCTCTGCTCTCCCCGGCTGCAGCCCAGCGCCACTCGGGCAGGCTTC

2510 ACACGCTCACCCCAGGTGGCCTCGGAACAGCTGCGACAGCATCTCCCCGCA

2561 CCCTTCTGCCTTCTCAGCACTTGGCTCTCCAGCCAGCCTCTCCACTCACTC

2612 GTTTTTGTTTCCCGGAGCTGTCTGCCACAATGTTGGCAGTCTTCATGGACT

2663 ACTGTACGTGATTCTGCTGAATTTTAAATAAATAAACCCTGCAAATCAAAA

2714 AAAAAAAAAAAAAAAA
```

Expression and characterization of HRI from the isolated cDNA.

The 5' untranslated leader sequence of the HRI cDNA was replaced by the use of PCR to introduce a unique NcoI site (CCATGG) at the initiating methionine (nt 113), followed by ligation of the coding sequence to a vector containing the tobacco mosaic virus (TMV) untranslated leader sequence which was engineered to provide both the initiating methionine and 3'-terminal NcoI site. The introduction of the NcoI site changes the second amino acid of HRI from leucine to valine, constituting a conservative substitution.

Linearized HRI cDNAs were transcribed using T7 polymerase. In vitro translation of HRI mRNA (40 μg/ml) was carried out in the presence of [$^{35}$S]-methionine as described by Promega using nuclease-treated reticulocyte lysates or wheat-germ extracts. Protein kinase assays were carried out in 40 μl reactions with 10 mCi of [g-$^{32}$P]ATP (3,000 Ci/mmol), 1.5 μl of translational mixture and purified rabbit eIF-2 (1 μg) as indicated, at 30° C. (reticulocyte lysate) or 25° C. (wheat germ extract) for 10 min as described by Chen, J. -J., et al., *J. Biol. Chem.*, 264:9559–9564 (1989).

In vitro transcription and translation were carried out in order to determine the apparent molecular size of the protein encoded by the HRI cDNA and to test for protein kinase activity. Translation of all five HRI clone mRNAs in a nuclease-treated rabbit reticulocyte lysate yielded a predominant 90 kDa product as observed by SDS-PAGE.

The nucleotide sequence data demonstrate that the 5' untranslated leader sequence is extremely G-C rich with the potential to form significant secondary structure. Secondary structure at the 5'-terminus of mRNAs is known to diminish mRNA translational efficiency. The HRI mRNA was not translatable in a wheat germ extract. Unlike the reticulocyte lysate, the wheat germ extract does not contain an endogenous HRI enzyme; therefore, expression of the HRI protein in the wheat germ system should facilitate analysis of kinase activity in the HRI translation products. The translational efficiency of mRNA transcripts can be increased by the use of untranslated leader sequences of some plant viral RNAs such as TMV have been shown to act in cis by Gallie, et al., (1987) *Nucl. Acids Res.*, 15, 8693–8711, and Gehrke, L. and Jobling, S. A., (1990) In: McCarthy, JEG *Post-Transcriptional Regulation of Gene Expression, Series H: Cell Biology*, ed. Tuite, M. (Springer Verlag, Berlin), Vol. 49, pp. 389–398. Accordingly, the G-C rich HRI untranslated leader sequence was replaced with that of TMV. The chimeric TMV-HRI mRNA was translated with approximately tenfold greater efficiency than HRI mRNA in the reticulocyte lysate, and translation in the wheat germ extract was clearly evident. In all cases, the translated product of HRI mRNA migrated slightly faster than authentic purified phosphorylated HRI on SDS gel electrophoresis. This slight difference in mobility is most likely due to a lower level of phosphorylation in the translation products.

To determine whether the translational product derived from the mRNA of HRI cDNA is an eIF-2α kinase, a small portion of the total translation mixture was incubated with purified rabbit reticulocyte eIF-2 and [g-$^{32}$P] ATP in the absence of added hemin under protein kinase assay conditions and analyzed by SDS-gel electrophoresis.

The results show that translational products of HRI 2A and HRI 2B mRNAs have enhanced eIF-2α kinase activity as compared to the control in the absence of added mRNA. It should be emphasized that under the kinase assay conditions (final hemin concentration of 0.75 μM) the activity of newly synthesized HRI exceeds the low activity of endogenous pre-formed HRI in the nuclease-treated lysate and makes it possible to detect enhanced phosphorylation of eIF-2α. In the absence of added purified rabbit eIF-2, only slight phosphorylation in the region of eIF-2α is observed. Furthermore, the HRI polypeptide synthesized in the wheat-germ extracts exhibits eIF-2α kinase activity as does purified HRI. It should be noted that there is no mammalian eIF-2α kinase activity in the wheat-germ extracts, and the purified reticulocyte HRI phosphorylates purified wheat germ eIF-2α very inefficiently. In addition, the 90 kDa polypeptide expressed from HRI cDNA is immunoprecipitated by monoclonal antibodies to HRI.

Isolation of cDNA encoding HRI in other mammalian species.

DNA nucleotide sequence data were analyzed in part using CAD Gene™ software for the Macintosh™ computer, provided by the Genetic Technology Corporation, Cambridge, Mass. The amino acid sequences of dsRNA-dependent eIF-2α kinase (dsI) of rabbit and human are 83% similar and 76% in identity. Similar or higher degree of homology of initiation factors (eIF-2α, and eIF-2β eIF-4A, eIF-4E, EF-1a) between human and rabbit has been demonstrated. The predicted homology of HRI between human and rabbit is greater than 80%. Accordingly, the sequence encoding HRI in human or other species can be isolated by hybridization under standard conditions such as those outlined by Maniatis, et al., (1989) *Molecular Cloning. A Laboratory Manual*, from a library prepared from reticulocytes of the other species. The isolated sequence can then be expressed in the same manner as the HRI cDNA isolated from rabbit reticulocytes as described below in the Examples.

High degree of homology between HRI and other protein kinases.

Purified non-recombinant HRI undergoes heme-regulated autophosphorylation and eIF-2α phosphorylation. The sites of autophosphorylation of many protein kinases are located within 20 amino acids of the conserved Ala/Ser-Pro-Glu sequence in catalytic domain VIII (e.g. Thr-197 of cAMP-dependent protein kinase). The HRI-equivalent of the Thr-197 of cAMP-dependent protein kinase is Thr-483. In addition, there are two serine and three more threonine residues in the vicinity of Thr-483. Since HRI can undergo multiple phosphorylation in vitro the availability of HRI cDNA will facilitate the further study of the sites and role of autophosphorylation in the activation of HRI.

Comparison of HRI and dsI and GCN2 protein kinase.

Figure 4A:
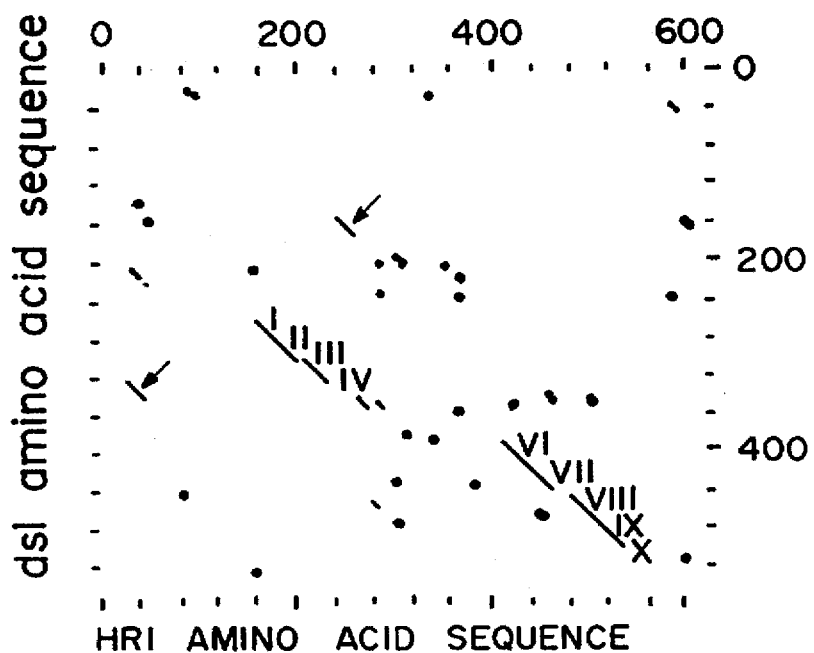
FIGS. 4A and B are dot-matrix analyses showing homology. (A) Dot-Matrix analysis of the amino acid sequences of HRI and GCN2. (B) Dot-Matrix analysis of the amino acid sequences of HRI and dsI. The dot-matrix was performed using Compare program of Maizel, J. V., Jr. and Lenk, R. P., Proc. Natl. Acad. Sci., USA 78:7665–7669 (1981), with window of 30 and stringency of 15. The locations of the conserved catalytic domains of protein kinases are indicated.

Comparison of the amino acid sequences of HRI and dsI deduced from the cDNAs indicates that in addition to general homology in kinase conserved domains, there is a very significant homology of both eIF-2α kinases around domains IX and X (HRI amino acid 511–540), as shown in FIG. 4A. It is likely that these amino acids are involved in eIF-2 binding and the phosphorylation of eIF-2α. In addition, HRI synthetic peptide P-74 which resides around domain IX inhibits the eIF-2α kinase activity of both HRI and dsI.

The Gene Bank has been searched for homology to other protein sequences of the amino acid sequence of HRI deduced from its cDNA. Of the ten proteins with the highest scores (Table I), nine are Ser/Thr protein kinases, and of these, three are involved in regulation of the cell cycle (Nim A, Wee1 and CDC2).

Figure 4B:
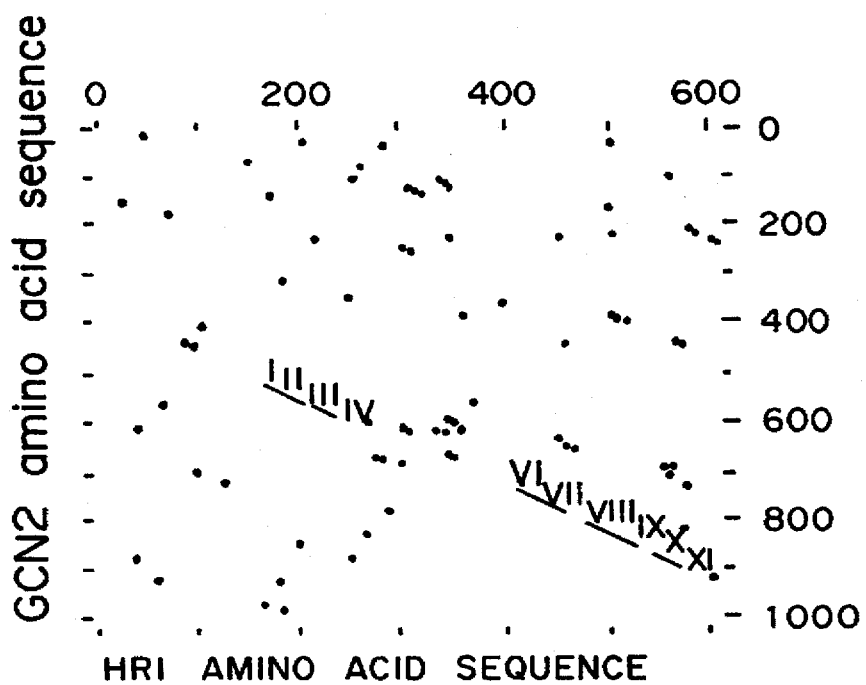

It is especially noteworthy that GCN2 protein kinase of yeast displays more homology to HRI than does dsI, the other known eIF-2α kinase (Table I). The scores of homology of HRI to GCN2 and dsI are significantly higher than those to other protein kinases (Table I). The cDNA of human dsI was recently cloned by Meurs, et al., (1990) *Cell*, 62:379–390. A dot-matrix homology analysis of HRI and dsI coding sequences is shown in FIG. 4A, and a similar analysis of HRI and the kinase moiety of GCN2 coding sequences is shown in FIG. 4B. These dot-matrix plots reveal the extensive homology of these three proteins in the protein kinase catalytic domains I through X except for domain V where HRI has a large kinase insertion sequence. Homology in domains IX and X is observed only with HRI, dsI and GCN2, but not with the other eight protein kinases with the best scores. The significant homology in these regions suggests that these amino acids may be involved in the binding and phosphorylation of eIF-2, and raise the possibility that GCN2 protein kinase may be an eIF-2α kinase in yeast.

TABLE 1

Homology of HRI to other Protein Kinases

| Kinase | Scores |
|---|---|
| GCN2 protein kinase (Yeast) | 383 |
| dsRNA-dependent eIF-2α kinase (Human) | 331 |
| Ca$^{+2}$/calmodulin protein kinase (Rat) | 252 |
| Never-in-Mitosis gene product (Yeast) | 249 |
| Wee 1 gene product (Yeast) | 246 |
| Type II Ca$^{+2}$/calmod kinase (Rat brain) | 222 |
| Calmodulin-dependent protein kinase (Rat) | 211 |
| Calmodulin-dependent protein kinase II (Rat) | 211 |
| M38724 Mus musculus cell cycle protein | 209 |
| Calmodulin-dependent protein kinase II (Rat) | 207 |
| CDC2 gene product (Human) | 206 |
| cAMP-dependent protein kinase (Yeast) | 205 |
| Protein kinase gene (Yeast) | 205 |
| M37712 p58/GTA protein kinase (Human) | 204 |
| cAMP-dependent kinase (Yeast) | 197 |
| TPK2 gene (Yeast) | 195 |
| *cAMP-dependent kinase | 194 |
| Protein Kinase C (Rat) | 192 |
| Protein kinase C zeta-subspecies (Rat) | 184 |
| CDC2 cell division gene (Yeast) | 184 |
| Varicella-Zoster virus complete genome | 181 |
| Muscle light *chain kinase (Rat) | 180 |
| HSV-2 genomic HindIII 1 region | 180 |

TABLE 1-continued

Homology of HRI to other Protein Kinases

| Kinase | Scores |
| --- | --- |
| Tyrosine kinase (Rat) | 180 |
| Src (Rat) | 180 |
| Tyrosine kinase (Human) | 176 |

The homology of the protein sequence of HRI to those of other proteins in Gene Bank was determined using Fast A program of Pearson, W. R. and Lipman, D. J., (1988) Proc. Natl. Acad. Sci., USA, 85:2444-2448.

GCN2 protein kinase of yeast displays very significant homology to HRI (Table I and FIG. 4B) especially in domains IX and X in which considerable homology is observed only in eIF-2α kinases. GCN2 protein kinase stimulates the expression of amino acid biosynthetic genes under conditions of amino acid starvation by derepressing GCN4, a transcriptional activator of these genes. The derepression of GCN4 by GCN2 protein kinase occurs at the level of translation of GCN4 mRNA. The activation of the translation of GCN4 mRNA coincides with a decrease in the rate of general polypeptide chain initiation at the level of eIF-2 dependent 43 S pre-initiation complex formation. Furthermore, a yeast strain that overexpresses GCN2 protein kinase has been reported to have a lower rate of protein synthesis. Thus, the effect of GCN2 protein kinase on protein synthesis is very similar to that of HRI. The molecular cloning of yeast eIF-2α by Cigan, et al., (1989) Proc. Natl. Acad. Sci., USA, 86:2784-2788, reveals 58% homology of its amino acid sequence to human eIF-2α, as reported by Ernst, et al., (1987) J. Biol. Chem., 262:1206-1212. In addition, consensus phosphorylation site Ser-51 is conserved in yeast eIF-2α, and the phosphorylation of yeast eIF-2α has been demonstrated by Cigan, et al. The possibility that GCN2 protein kinase may phosphorylate eIF-2 has been raised by Cigan et al and Tzamarias et al, (1989) Cell, 57:947-954. The alignment of the amino acid sequences of HRI and GCN2 indicates 52% similarity and 28% identity in the kinase moiety of GCN2. This extensive homology of HRI and GCN2 affords further support for the view that GCN2 may be an eIF-2α kinase in yeast. Recently, it has been demonstrated that phosphorylation of e2F-2α is required for the translational control of yeast GCN4, Dever, et al., Cell 68, 585-596 (1992).

Comparison of unique insertion sequence.

As shown in FIG. 4, HRI cDNA contains an insertion of approximately 140 amino acids between catalytic domains V and VI (amino acids 276 to 413). Similar large inserts have been reported for subclass III and IV receptor tyrosine kinases, which include the PDGF receptor, the CSF-1 receptor and the c-kit proto oncogene product, in which the kinase domains are divided into two halves by insertion of up to 100 mostly hydrophilic amino acid residues, as reviewed in Ullrich, A. and Schlessing, J., (1990) Cell, 61:203-212. Since kinase insertion sequences are highly conserved among species for each specific receptor, the kinase insert may play an important role in the action of receptor kinases. Indeed, the PDGF receptor kinase insert contains an autophosphorylation site (Tyr-751), and mutation of Tyr-751 to Phe or Gly blocks association of the PDGF receptor with phosphatidylinositol kinase and three other cellular proteins. In the case of HRI, heme binds to HRI and regulates its kinase activities. It is believed that the kinase insertion sequence of HRI is involved in the binding of heme and the regulation of the autokinase and eIF-2α kinase activities.
Comparison of HRI and protein kinases involved in the cell cycle.

There is also a high degree of homology between HRI and several protein kinases involved in the cell cycle.

Hanks, Quinn and Hunter (1988) Science, 241:42-52, have compared and aligned the protein sequences of 65 different protein kinases. They have identified eleven domains of protein kinases with invariant amino acid residues in each domain. The alignment of the HRI sequence with the sequences of a serine/threonine protein kinase ($Ca^{++}$/calmodulin protein kinase) and of a tyrosine protein kinase (Src) is shown in FIG. 3. HRI cDNA contains all eleven catalytic domains with invariant amino acid residues, as also shown in FIG. 4. The consensus ATP-binding sequence, Gly-X-Gly-X-X-Gly, and the invariant valine residue located two positions downstream of the Gly-X-Gly-X-X-Gly are conserved in HRI. In domain II, the invariant Lys residue has been shown to be indispensable and to be involved in the phosphotransferase activity of protein kinases. In HRI this invariant residue is Lys-199. Domain VI contains the consensus sequence which specifies either Ser/Thr protein kinases or Tyr protein kinases. HRI possesses Asp-Leu-Lys-Pro-Arg-Asn in domain VI which is characteristic of Ser/Thr protein kinases. Asp-Phe-Gly located in domain VII is the most conserved short stretch in the catalytic domains of protein kinases and is probably involved in ATP-binding. It is found in HRI as Asp(-456)-Phe(-457)-Gly(-458). In domain VIII the Ala/Ser-Pro-Glu consensus sequence essential for catalytic activity of protein kinases is also found in HRI. Domain VIII of HRI contains the other consensus sequence for Ser/Thr protein kinases, Gly-Thr-Cys-Leu-Tyr. The conserved amino acids in domain IX are also found in HRI. Thus, the homology of the deduced amino acid sequence of HRI cDNA to the conserved domains of other Ser/Thr protein kinases provides confirmatory evidence that HRI cDNA encodes a Ser/Thr protein kinase.

Inhibition of Cell Proliferation and Differentiation and viral activity and the induction of Differentiation using HRI or dsI.

Since HRI is a potent inhibitor of protein synthesis, it is anti-proliferative in nature and should be useful in the treatment of various cancers in which uncontrolled cell growth persists, for example chronic myelogenous leukemia. HRI should also be useful in treatment of other proliferative disorders such as psoriasis.

Initiation of protein synthesis can also be regulated by another eIF-2α kinase which is activated by double-stranded RNA (dsI). Both HRI and dsI phosphorylate eIF-2α at the same site. However, HRI and dsI are different molecules. dsI is induced by interferon and represents an interferon mediated response to viral infection. However, mechanisms of inactivating dsI have evolved in various viruses to undermine the anti-viral action of dsI. Since HRI and dsI are both eIF-2α kinases, both should be anti-viral in nature. However, mechanisms of inactivating viruses by dsI should not similarly affect HRI activity. Therefore, when introduced into the proper target cell, HRI may be as potent or more potent than dsI as an anti-viral agent.

Based on the similarity to proteins involved in cellular differentiation, it is expected that HRI will induce differentiation. As noted above, CDC2, Wee 1 and Nim A contain consensus sequences for serine/threonine protein kinases. They were identified first in yeast by genetic means. However, CDC2 and Wee 1 have also been isolated and characterized in human cells. The CDC2 gene product is required for both S phase and mitosis. The Wee 1 gene product is an inhibitor of mitosis. Nim A gene product is an activator of mitosis. Both Nim A and Wee 1 gene products regulate the cell cycle through regulation of CDC2 kinase which is part of the mitosis promoting factor. Many types of cancers are characterized by arrested differentiation. HRI can also be introduced into these cells to induce differentiation and thereby limit the proliferation of the transformed cells.

Since HRI is expressed normally only in very small quantities, in the cytoplasm, and during specific periods of erythroid differentiation, small quantities of the protein are expected to be effective in inhibiting protein synthesis, inducing differentiation, and inhibiting infection by viruses and parasites.

The HRI, expressed from the cDNA, preferably of the same species as the cells to be treated, can be administered topically, by injection, or via implant to the cells or patient to be treated. Appropriate pharmaceutical compositions and methods for administration and use thereof are well known to those skilled in the art. The HRI can be expressed in any suitable mammalian expression system, using known technology, under the control of appropriate enhancers and promoters.

Alternatively, the cells to be treated are "infected" with the sequence encoding the HRI. In the preferred embodiment, this is accomplished by inserting the HRI sequence into a retroviral vector with which the cell is then infected. For example, a retroviral vector for gene transfer and expression of HRI cDNA can be constructed using as the backbone of the retroviral vector the LNCX vector described by Miller and Rosman (Miller, A. D., and Rosman, G. J. (1989) *BioTechniques* 7:980–990). It contains human cytomegalovirus (CMV) immediate early gene promoter and enhancer. HRI cDNA containing TMV-leader sequence is introduced into the LNCX vector through a polylinker region downstream from the CMV promoter.

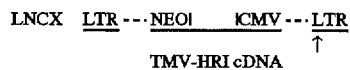

```
LNCX   LTR---NEOI    ICMV---LTR
                         ↑
             TMV-HRI cDNA
```

Gene transfer by retroviral vector can also be achieved by transfection by a viral vector, using the method of Wilson, J. M., Biriuyi, L. U., Salomon, R. U., et al. Transplantation of Vascular Grafts Lined With Genetically Modified Endothelial Cells. *Science*, 244:1344–1346 (1980), or a plasmid transfer technique, as described by Felgner, P. L., Galik, T. R., Holmer, et al. Lipofection: An Efficient, Lipid Mediated DNA-Transfection Procedures. *Proc. Natl. Acad. Sci.*, 84:7413–7417 (1987), the teachings of which are incorporated herein by reference.

Specifically, cells are harvested, grown to subconfluence (60–70%) and incubated with a replication defective murine Moloney leukemia retroviral vector. The DNA sequence for HRI is inserted into the viral genome and is under the promoter control of the viral long-terminal repeats (LTR's). The infected cells are trypsinized, resuspended in saline containing penicillin (100 U/ml) and streptomycin (100 µg/ml) and transplanted into the patient requiring treatment. The presence of HRI in the culture medium or the site of transplantation can be determined by radioimmunoassay.

Construction of deletion mutants of HRI cDNA that are insensitive to heme, less species specific or overexpressed.

Deletion mutants of HRI cDNA which are not sensitive to regulation by heme can be constructed, based on the prediction that the heme-binding region is found within the HRI-specific insert discussed above and/or in the 170 N-terminal amino acids. This heme-insensitive HRI may be more effective than native HRI in its anti-viral and anti-proliferative action.

Deletion mutants of HRI cDNA can also be constructed which are less species specific. There is greater than 80% homology between species (86% between human and rabbit dsI). The primary area of species variation is in domain V. Methods for constructing and screening for these mutations are known to those skilled in the art.

EXAMPLE 1

Expression of HRI mRNA in Human and Mouse Erythroid Cells.

Figure 5A:
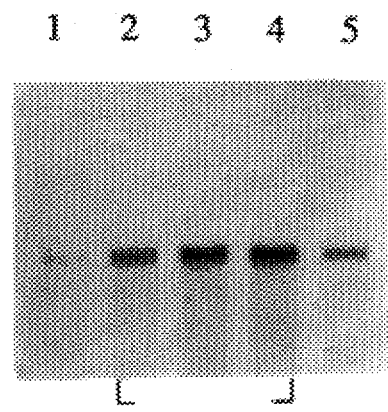
FIG. 5A is a photograph of a Northern blot showing expression of HRI mRNA in mouse erythroid cells, using as the probe rabbit HRI cDNA from nucleotides 113 to 2149 (all HRI coding sequences and 159 nucleotides of 3' noncoding sequence).
Figure 5B:
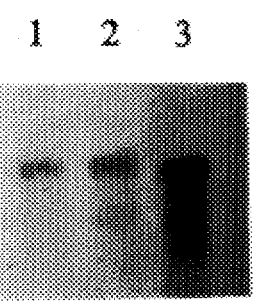
FIG. 5B is a photograph of a Northern blot showing expression of HRI mRNA in human erythroid cells, using the same probe as in FIG. 5A.

The expression of HRI mRNA in human erythroleukemia cells (K562) and mouse friend erythroleukemia cells (MEL) during erythroid differentiation was examined by Northern-Blot analysis. The probe used for the Northern-Blot analysis shown in FIGS. 5A and 5B is the above-described rabbit HRI cDNA from nucleotides 113 to 2149 which is comprised of all the coding sequences of HRI cDNA and 159 nucleotides of the 3' non-coding sequence. The results in FIGS. 5A and 5B show that rabbit HRI cDNA hybridizes to a 3.1 Kb mRNA from both MEL (Panel A) and K562 (Panel B) cells. The HRI mRNA from K562 and MEL cells appears to be of the same size as rabbit HRI mRNA. In addition, HRI mRNA is increased upon erythroid differentiation induced by incubation of cells with hemin for four days.

Cell Culture

K562 cells were maintained in RPMI 1640 medium containing 10% fetal calf serum and antibiotics at 37° C. in 5% $CO_2$. Cells were treated with 75 mM hemin by dilution of a 1 mM hemin stock solution directly into the culture medium. After four days, the cells were washed twice in culture medium and incubated in their normal growth medium for 12 hours. The cells were then collected and washed twice in phosphate buffered saline (PBS). MEL cells were grown in Dulbeco modified minimum essential medium containing 10% fetal calf serum. Cells were induced for erythroid differentiation by the addition of 2% dimethylsulfoxide (DMSO). Cells were harvested 3, 4 and 5 days after DMSO-treatment as described above.

mRNA Isolation and Northern Blotting

Poly $(A)^+$ mRNA was isolated from both untreated K562 cells, hemin treated K562 cells, untreated MEL cells and DMSO-treated MEL cells using oligo (dT) cellulose and an Invitrogen™ mRNA Isolation Kit. $1 \times 10^8$ cells consistently yielded 15–20 µg of high quality mRNA. 5 µg of each sample mRNA were denatured and separated on 1.0% agarose formaldehyde denaturing gels. mRNA was transferred to a nitrocellulose membrane in 20× SSPE overnight at room temperature and cross-linked to the nitrocellulose by UV irradiation.

Hybridization

Nitrocellulose filters were prehybridized in 50% formaminde, 6× SSPE, 5× Denhardt's solution, 0.5% SDS, 100 mg/ml salmon sperm DNA and 10% dextran sulfate, at 42° C. for overnight (12–14 hrs). Hybridization took place under the same conditions but for the addition of $1-3 \times 10^9$ cpm/µg $^{32}$P-labeled HRI cDNA. Nitrocellulose filters were washed 3 times for 5 minutes in 2× SSPE+0.1% SDS at room temperature (R.T.), followed by washes of 1× SSPE+ 0.1% SDS for 10 minutes at room temperature, 1× SSPE+ 0.1% SDS for 10 minutes at 50° C., and 0.2× SSPE+0.1% SDS for 10 minutes, 50° C. Membranes were exposed to film (Kodak X-AR) at −80° C. with an intensifying screen.

EXAMPLE 2

Amplification of Human HRI cDNA Sequence Using Rabbit HRI cDNA Sequence.

Figure 6:
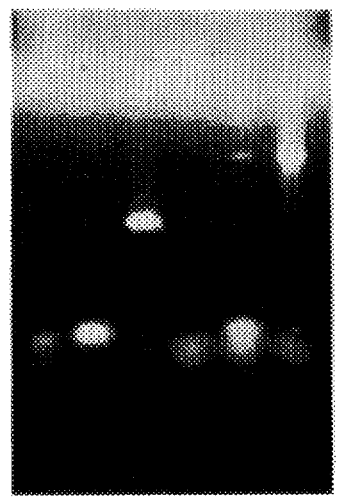
FIG. 6 is a photograph of an agarose gel showing amplification of a human HRI cDNA sequence using the rabbit HRI cDNA sequence: lanes 1–3, primers were nucleotides 229–249 and 543–560; lanes 4–6, primers were nucleotides 448–468 and 1009–1031.

Several oligonucleotides of the above-described rabbit HRI cDNA were used as primers for the polymerase chain reaction (PCR) to amplify the human HRI cDNA sequence. The poly A⁺ mRNAs from hemin-induced K562 cells was reversed-transcribed to obtain single-stranded cDNAs. This single-stranded cDNA preparation was used as a template to amplify a human HRI cDNA sequence. The primers used for PCR reactions shown in Lanes 1 to 3 of FIG. 6 are nucleotides 229–249 and nucleotides 543–560. An expected DNA fragment of 331 bp was amplified from cloned HRI cDNA 2B of rabbit (Lane 3). A faint but detectable DNA fragment of the same size was also amplified from the cDNA reversed-transcribed from human K562 poly A⁺ mRNA (Lane 2), but not from human HeLa cells (Lane 1). The primers used for PCR reactions shown in Lanes 4 to 6 are nucleotides 448–468 and nucleotides 1009 to 1031. An expected DNA fragment of 584 bp was amplified from cloned rabbit HRI cDNA 2B (Lane 6) and from human K562 cDNA (Lane 5). These two amplified human HRI cDNA fragments are located in the N-terminus of HRI coding sequence where conserved sequences of protein kinase are not found. The lack of homology of the N-terminus of HRI to other nucleotide sequences is shown in Table 2. The N-terminus of protein kinases is usually devoted to a regulatory role of a particular protein kinase. The result of a search of the GeneBank database indicates that the first 170 amino acids of the N-terminus of HRI is unique to HRI; no significant homology to other eIF-2α kinases (GCN2 and dsI) is observed. Therefore, the amplification of human HRI cDNA sequences from rabbit HRI cDNA shown in FIG. 6 is very significant and demonstrates the extensive homology of human HRI cDNA to rabbit HRI cDNA. The human HRI cDNA sequence in the conserved domains from domain VII to domain IX was also amplified.

TABLE 2

Non-Homology of N-terminus of HRI to other Kinases

| Kinase | Scores |
| --- | --- |
| Varicella-Zoster virus complete genome | 100 |
| Skeletal muscle voltage-sensitive Na+ channel (Rat) | 96 |
| Cytomegalovirus (HCMV) (Human) | 92 |
| Foot and Mouth Disease Virus | 92 |
| Adenylate cyclase gene | 90 |
| cGMP-dependent protein kinase (D. melanogaster) | 88 |
| Mesothelial keratin K7 (type II) (Human) | 88 |
| Mei2 gene (Human) | 86 |

The non-homology of the protein sequence of the N-terminal of HRI to other sequences in Gene Bank was determined using Fast A program of Pearson, W. R. and Lipman, D. J., (1988) Proc. Natl. Acad. Sci., USA, 85:2444–2448.

The results of FIGS. 5A, 5B and 6 demonstrate that HRI cDNA from species other than rabbits, including humans, can be cloned using rabbit HRI cDNA from a cDNA library of hemin-treated K562 cells.

Modifications and variations of the present invention, the methods of use of cDNA encoding HRI will be obvious to those skilled in the art from the foregoing detailed description. Such modifications and variations are intended to come within the scope of the following claims.

We claim:

1. A pharmaceutical composition comprising heme-regulated eukaryotic initiation factor 2α kinase in combination with a suitable pharmaceutical carrier for administration to cells.

2. The pharmaceutical composition of claim 1 wherein the kinase consists of the amino acid sequence of Sequence Listing ID No. 2.

3. The composition of claim 1 wherein the first 170 amino acids of the kinase are encoded by a DNA sequence consisting of nucleotides 113 to 622 of Sequence Listing ID No. 1.

4. A method for inhibiting protein synthesis, inducing cellular differentiation, or inhibiting infection comprising administering to cells to be treated an effective amount of a heme-regulated eukaryotic initiation factor 2α kinase in combination with a suitable pharmaceutical carrier for administration to the cells.

5. The method of claim 4 wherein the kinase is expressed from a nucleic acid molecule which specifically hybridizes to primers consisting of nucleotides 229–249, 448–468, 543–560 or 1009–1031 of Sequence Listing ID No. 1.

6. The method of claim 4 wherein the first 170 amino acids of the kinase are encoded by a DNA sequence consisting of nucleotides 113 to 622 of Sequence Listing ID No. 1.

7. The method of claim 4 wherein the kinase consists of the amino acid sequence of Sequence Listing ID No. 2.

8. The method of claim 4 wherein the first 170 amino acids of the kinase are encoded by a DNA sequence consisting of nucleotides 113 to 622 of Sequence Listing ID No. 1.

9. The method of claim 4 wherein the kinase is administered to cells characterized by abnormally fast proliferation for that cell type.

10. The method of claim 9 wherein the cells are cancerous.

11. The method of claim 9 wherein the cells are in a patient suffering from psoriasis.

12. The method of claim 4 wherein the cells are infected or exposed to infection by a virus.

* * * * *